(12) United States Patent
Akiyama et al.

(10) Patent No.: US 6,426,631 B1
(45) Date of Patent: Jul. 30, 2002

(54) OXYGEN SENSOR DEVICE INCORPORATING A HEATER THEREIN

(75) Inventors: Masahide Akiyama; Hiroshi Ono; Hitoshi Matsunosako, all of Kokubu (JP)

(73) Assignee: Kyocera Corporation, Kyoto (JP)

( * ) Notice: Subject to any disclaimer, the term of this patent is extended or adjusted under 35 U.S.C. 154(b) by 0 days.

(21) Appl. No.: 09/560,944

(22) Filed: Apr. 28, 2000

(30) Foreign Application Priority Data

| Apr. 28, 1999 | (JP) | ............................................ | 11-121342 |
| Jul. 30, 1999 | (JP) | ............................................ | 11-218058 |
| Dec. 22, 1999 | (JP) | ............................................ | 11-365022 |
| Jan. 31, 2000 | (JP) | ............................................ | 2000-027279 |
| Mar. 29, 2000 | (JP) | ............................................ | 2000-092183 |

(51) Int. Cl.[7] ........................ G01N 27/62; G01N 27/26; F02M 7/00

(52) U.S. Cl. ........................ 324/464; 123/438; 204/406; 204/424

(58) Field of Search ................................ 324/464, 668, 324/698; 123/438, 688; 204/406, 408, 410

(56) References Cited

U.S. PATENT DOCUMENTS 5,698,084 A * 12/1997 Weyl et al. ................. 204/424

* cited by examiner

Primary Examiner—N. Le
Assistant Examiner—James Kerveros
(74) Attorney, Agent, or Firm—Hogan & Hartson, L.L.P.

(57) ABSTRACT

An oxygen sensor device consisting a cylindrical tube of a ceramic solid electrolyte having an oxygen ion conducting property, a reference electrode formed on an inner surface of the cylindrical tube, and a measuring electrode formed on an outer surface of the cylindrical tube at a position at least opposed to the reference electrode, wherein a ceramic layer is formed on the outer surface of the cylindrical tube, the ceramic layer having an opening portion for exposing the surface of the measuring electrode and incorporating a heat-generating member therein, the heat-generating member being buried surrounding the opening portion. The oxygen sensor device as a whole has a cylindrical shape relaxing the concentration of thermal stress and exhibiting excellent thermal shock resistance. With the heat-generating member being buried near the sensing portion, the sensing portion is heated up to a predetermined activating temperature within short periods of time exhibiting an excellent sensor response.

14 Claims, 17 Drawing Sheets

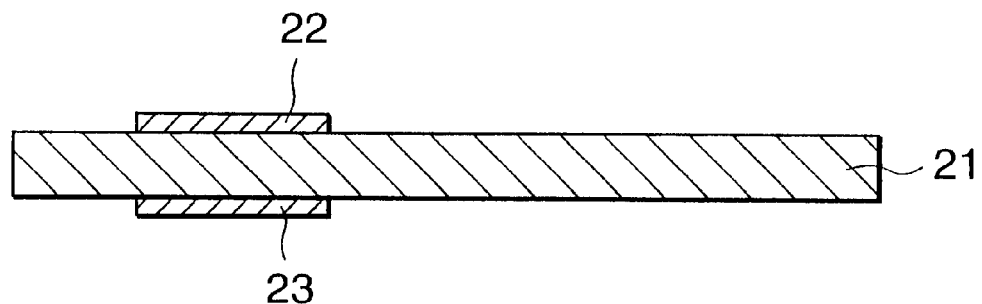
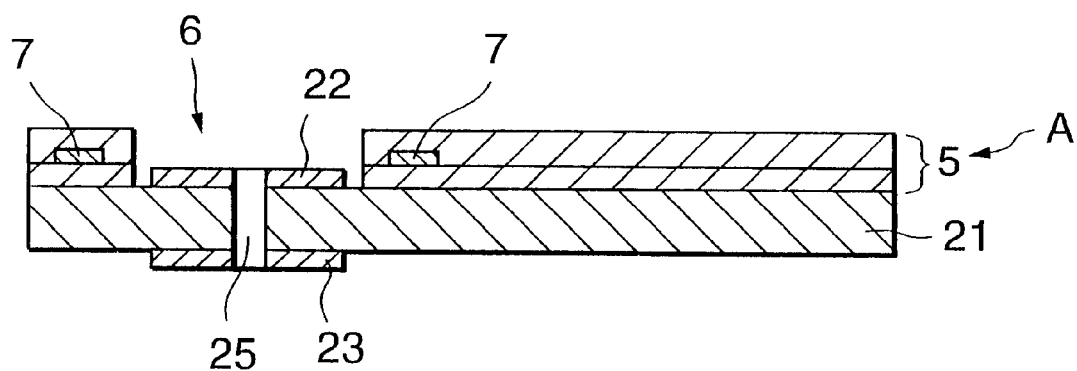

OXYGEN SENSOR DEVICE INCORPORATING A HEATER THEREIN

BACKGROUND OF THE INVENTION

1. Field of the Invention

The present invention relates to an oxygen sensor device used for controlling an air-fuel ratio in an internal combustion engine such as of automobiles. More specifically, the invention relates to an oxygen sensor device incorporating a heater therein and is capable of detecting the concentration of oxygen within a very short period of time.

2. Description of the Prior Art

Modern internal combustion engines of automobiles are employing a method of detecting the concentration of oxygen in the exhaust gas, and controlling the amounts of the air and fuel supplied into the internal combustion engine based on the detected value, in order to decrease harmful substances such as CO, HC and NOX emitted from the internal combustion engine.

As a device for detecting the concentration of oxygen, there has heretofore been known a cylindrical oxygen sensor device of the indirectly heated type having a structure as shown in, for example, FIG. 18. The oxygen sensor device is constituted by a cylindrical tube 31 made of a solid electrolyte such as zirconia having oxygen ion conducting property with its one end being closed. On the inner surface of the cylindrical tube 31 is provided a reference electrode 32 that comes in contact with a reference gas such as the air. On the outer surface of the cylindrical tube 31 is formed a measuring electrode 33 that comes in contact with a gas to be measured such as exhaust gas. Further, on the surface of the measuring electrode 33 is formed various porous ceramic layers 34 depending upon the use of the oxygen sensor device.

In, for example, a so-called stoichiometric air-fuel sensor ($\lambda$ sensor) used for controlling the air-fuel ratio (A/F ratio) near 1, the porous ceramic layer 34 formed on the surface of the measuring electrode 33 works as a protection layer, and a difference in the oxygen concentration between the inner surface and the outer surface of the cylindrical tube 31 is detected at a predetermined temperature to control the A/F ratio in the engine intake system.

On the other hand, in a so-called wide-range air-fuel ratio sensor (AF sensor) used for controlling the A/F ratio over a wide range, the porous ceramic layer formed on the surface of the measuring electrode 33 contains fine pores and works as a gas diffusion rate-determining layer, and in which a voltage is applied to the cylindrical tube 31 of a solid electrolyte through a pair of electrodes 32 and 33, and a limit current that is obtained is measured to control the A/F ratio in a lean burn region.

In either the above-mentioned $\lambda$ sensor or AF sensor, the sensing portion (where the reference electrode 32 and the measuring electrode 33 are provided) must be heated up to an operation temperature of about 700° C. For this purpose as shown in FIG. 18, a rod-like heater 35 is inserted in the inner space of the cylindrical tube 31 to heat the sensing portion up to the operation temperature (activating temperature).

In recent years, strict regulations have been enforced against the exhaust gases and, hence, it has been urged to detect CO, HC and NOx from immediately after the start of the engine. With the cylindrical oxygen sensor device of the indirectly heating type in which the above-mentioned heater 35 is inserted in the cylindrical tube 31, however, an extended period of time (activating time) is required before the sensing portion is heated up to the activating temperature leaving a problem in that regulations against the exhaust gases cannot be coped with to a sufficient degree.

To solve this problem, Japanese Unexamined Utility Model Publication (Kokai) No. 199666/1986 proposes a flat plate-type oxygen sensor device incorporating a heater as shown in FIG. 19. In this oxygen sensor device, space for a reference gas is formed in a solid electrolyte 39 of a flat plate, a measuring electrode 37 and a reference electrode 38 are formed on the outer surface and on the inner surface of a flat wall 36 of the solid electrolyte 39, and a heater 42 is integrally laminated on the solid electrolyte 39. The heater 42 is constituted by a ceramic insulating board 40 of a flat plate in which a heat-generating member 41 is buried.

Further, Japanese Unexamined Patent Publication (Kokai) No. 206380/1998 proposes a cylindrical oxygen sensor device incorporating a heater therein. In this oxygen sensor device like the oxygen sensor device of FIG. 18, a reference electrode and a measuring electrode are provided on the inner surface and on the outer surface of the cylindrical tube of a solid electrolyte, but having a gas-permeable porous insulating layer formed on the surface of the measuring electrode and a platinum heat-generating member provided in the insulating layer where the gas-permeability is low.

Unlike those of the conventional indirectly heated type, the above-mentioned flat-plate or cylindrical oxygen sensor incorporating a heater can be quickly heated owing to its direct-heating system, and the sensing portion can be quickly activated.

However, the oxygen sensor device incorporating a heater shown in FIG. 19 has poor durability and heat resistance due to its flat-plate shape, and is liable to be broken during the operation.

The oxygen sensor device incorporating a heater proposed in Japanese Unexamined Patent Publication (Kokai) No. 206380/1998 is manufactured by forming a cylindrical solid electrolytic portion by firing, forming the electrodes by plating or sputtering, and forming the insulating layer by plasma melt-injection method. In other words, this oxygen sensor device is produced by a complex method through an increased number of steps accompanied by such problems as poor yield and increased manufacturing cost. Besides, since a porous insulating layer is formed on the whole surface of the measuring electrode while burying the heat-generating member in the insulating layer, the junction strength of the heater portion is small lacking durability and heat resistance.

SUMMARY OF THE INVENTION

It is therefore an object of the present invention to provide an oxygen sensor device incorporating a heater therein, which can be activated within a short period of time, exhibits excellent durability and heat resistance, and can be easily produced.

According to the present invention, there is provided an oxygen sensor device comprising:

a cylindrical tube of a ceramic solid electrolyte having an oxygen ion conducting property and with its one end being closed;

a reference electrode formed on an inner surface of said cylindrical tube; and a measuring electrode formed on an outer surface of said cylindrical tube at a position at least opposed to said reference electrode; wherein a ceramic layer is formed on the outer surface of said cylindrical tube, said ceramic layer having an opening portion and incorporating a heat-generating member therein;

said opening portion in said ceramic layer is formed at such a position that said measuring electrode is at least partly exposed therein; and said heat-generating member is buried in said ceramic layer at a position at least near said measuring electrode.

In the oxygen sensor device of the invention, the outer surface of the cylindrical tube of the solid electrolyte is covered with the ceramic layer incorporating a heat-generating member therein and, besides, the heat-generating member is arranged near the measuring electrode (e.g., around the opening portion that works as a sensing portion). According to the present invention, therefore, the sensing portion is very efficiently heated by the heat-generating member and is quickly heated making it possible to shorten the time (activating time) until the activating temperature is reached. Besides, even compared with the conventional flat-plate type oxygen sensor device incorporating a heater shown in FIG. 19, the oxygen sensor device of the invention greatly shortens the activating time and exhibits excellent sensor response, since the heat-generating member has been arranged near the sensing portion.

In the oxygen sensor device of the invention, further, the ceramic layer incorporating the heater has a cylindrical shape which is integral with the cylindrical tube, exhibiting a large strength against stress from any direction and building up less stress therein compared with the flat-plate type oxygen sensor device incorporating the heater, and exhibits excellent heat resistance and durability.

Further, the oxygen sensor device of the invention can be produced by co-firing the cylindrical tube of the solid electrolyte and the ceramic layer incorporating the heat-generating member. Therefore, the oxygen sensor device of the invention is produced at a very decreased cost and is excellent even from the standpoint of economy as compared with the conventional oxygen sensor device obtained by separately preparing the oxygen sensor and the heater, and inserting the heater in the oxygen sensor.

Upon forming a porous ceramic layer on the surface of the measuring electrode, the oxygen sensor device incorporating a heater of the invention can be used as a stoichiometric A/F ratio sensor ($\lambda$ sensor) or a wide-range A/F ratio sensor (AF sensor).

BRIEF DESCRIPTION OF THE DRAWINGS

FIG. 1b is a sectional view of the oxygen sensor device along X1—X1 in FIG. 1a;

FIG. 3b is a sectional view of the oxygen sensor device along X3—X3 in FIG. 3a;

FIG. 6b is a sectional view of the oxygen sensor device along X6—X6 in FIG. 6a;

FIGS. 11a and 11b are views illustrating a process for producing a ceramic sheet (ceramic laminated sheet to be wound on a cylindrically molded article) used for producing the oxygen sensor device shown in FIGS. 6a and 6b;

DETAILED DESCRIPTION OF THE INVENTION

The invention will now be described in detail by way of embodiments in conjunction with the accompanying drawings.

Figure 1A:
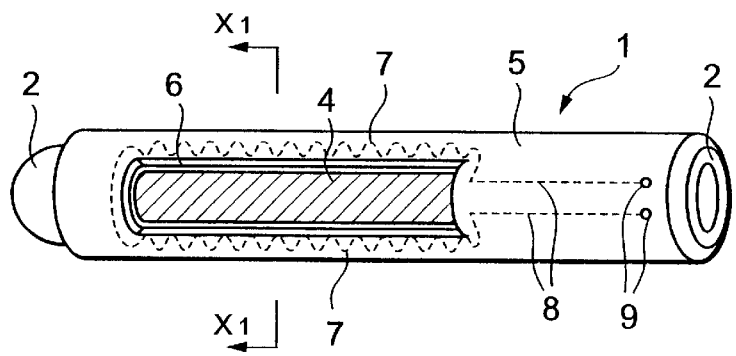
FIG. 1a is a perspective view schematically illustrating an oxygen sensor device of the present invention.
Figure 1B:
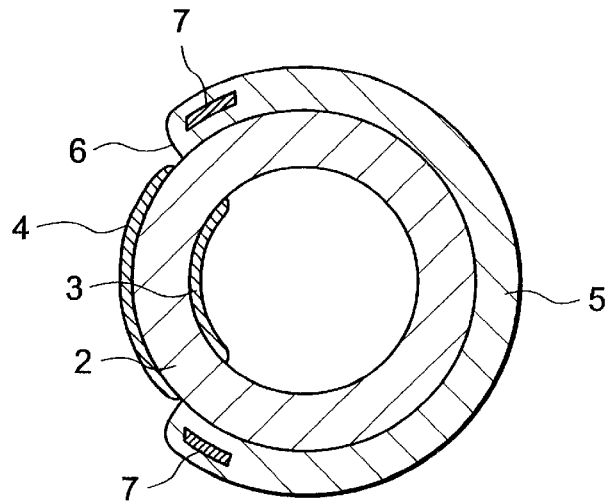

Referring to FIGS. 1a and 1b illustrating a representative example of the oxygen sensor device of the invention, the oxygen sensor device 1 is provided with a cylindrical tube 2 (having a U-shape in vertical cross section) made of a ceramic solid electrolyte having an oxygen ion conducting property with its end being closed. In the inner surface of the cylindrical tube 2 is formed by deposition a reference electrode 3 that comes in contact with a reference gas such as the air. On the outer surface of the cylindrical tube 2 is formed by deposition a measuring electrode 4 at a portion opposed to the reference electrode 3, the measuring electrode 4 coming in contact with a gas to be measured such as exhaust gas.

In this invention, a ceramic layer 5 incorporating a heat-generating member 7 therein is formed by deposition on the outer surface of the cylindrical tube 2. In the ceramic layer 5 incorporating the heat-generating member is formed an opening portion 6 in a manner that the measuring electrode 4 is partly or entirely exposed, and the heat-generating member 7 is buried near the opening portion 6. The heat-generating member 7 is connected to terminal electrodes 9 through lead electrodes 8. An electric current is supplied to the heat-generating member 7 through them to heat the heat-generating member 7 in order to quickly heat a sensing portion constituted by the measuring electrode 4, cylindrical tube 2 and reference electrode 3 up to a predetermined temperature.

The oxygen sensor device 1 as a whole has an outer diameter of, usually, from 3 to 6 mm and, particularly, from 3 to 4 mm.

(Cylindrical Tube 2)

The ceramic solid electrolyte used as a material for forming the cylindrical tube 2 of the invention has an oxygen ion conducting property and, usually, contains zirconia as a main component. Concretely speaking, a partly stabilized zirconia powder or a stabilized zirconia powder containing an oxide of a rare earth element, such as $Y_2O_3$, $Yb_2O_3$, $Sc_2O_3$, $Sm_2O_3$, $Nd_2O_3$ or $Dy_2O_3$ as a stabilizer in an amount of from 1 to 30 mol % or, preferably, from 3 to 15 mol % calculated in terms of an oxide, is favorably used as a ceramic solid electrolyte for forming the cylindrical tube (the oxide of rare earth element used as a stabilizer is for imparting an oxygen ion conducting property). It is also possible to form the cylindrical tube 2 by using a co-precipitating starting powder of zirconia and the above stabilizer.

Upon substituting 1 to 20 atomic % of Zr in the zirconia ($ZrO_2$) with Ce, further, the electron conducting property increases and the sensor response is further improved.

In order to improve the sintering property, further, the cylindrical tube 2 may be produced while adding a sintering assistant such as $Al_2O_3$ or $SiO_2$ to $ZrO_2$. However, use of the sintering assistant in large amounts deteriorates the creeping property at high temperatures. It is therefore desired that the sintering assistant is used in an amount of not larger than 5% by weight and, particularly, not larger than 2% by weight.

It is desired that the cylindrical tube 2 made of the ceramic solid electrolyte has a thickness of, usually, from about 200 $\mu$m to about 2 mm.

Further, the cylindrical tube 2 that is closed at its one end has any shape, such as spherical shape, cylindrical shape or a tapered shape becoming thin toward the end, and any shape may be suitably selected by taking the strength and easiness of production of the sensor into consideration.

(Ceramic Layer 5 Incorporating a Heat-Generating Member)

As the ceramic layer 5 incorporating the heat-generating member 7, there can be favorably used an insulating ceramic material such as alumina, spinel, forsterite, glass or the like. When the ceramic layer 5 is to be formed by using a glass, in particular, it is desired to use a glass containing at least any one of BaO, PbO, SrO, CaO and CdO in an amount of not less than 5% by weight and, particularly, a crystallized glass from the standpoint of heat resistance.

Figure 2:
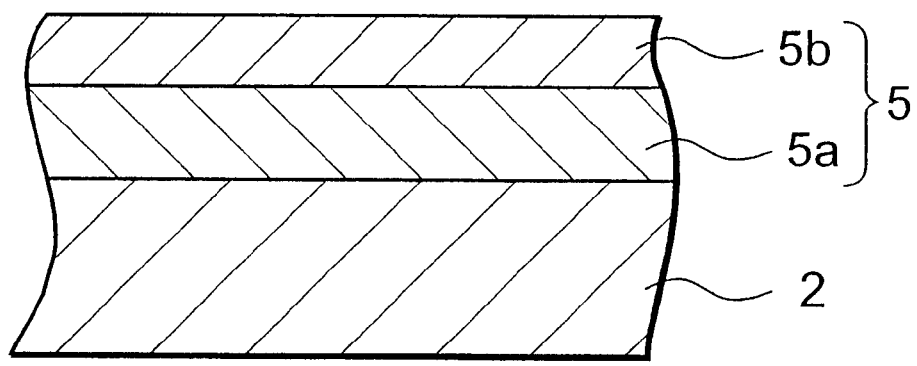
FIG. 2 is a sectional view illustrating the structure of ceramic layers incorporating a heat-generating member.

It is also allowable to from the ceramic layer 5 by using a solid electrolytic ceramic such as zirconia. The ceramic layer 5 that is formed by using zirconia relaxes the stress stemming from a difference in the thermal expansion or stemming from a difference in the contraction due to firing between the cylindrical tube 2 of the solid electrolyte and the ceramic layer 5, minimizes the thermal stress, maintains the heat generated by the heat-generating member 7 buried in the ceramic layer 5, and prevents a sudden change in the temperature in the oxygen sensor device as a whole. When the zirconia which is a solid electrolyte is to be used, however, it is desired that the ceramic layer 5 is constituted by an insulating layer 5a of the above-mentioned insulating ceramic and a zirconia layer 5b as shown in FIG. 2, and has the insulating layer 5a interposed between the zirconia layer 5b and the cylindrical tube 2.

In the present invention, it is desired that the ceramic constituting the ceramic layer 5 incorporating the heat-generating member is highly dense having a relative density of, for example, not smaller than 80% and an open porosity of not larger than 5%. This is because, the ceramic layer 5 having a high density exhibits an increased strength, enabling the oxygen sensor device 1 itself to exhibit an increased mechanical strength.

There is no particular limitation on the thickness of the ceramic layer 5 so far as it is capable of completely burying the heat-generating member 7 that will be described later therein. When the ceramic layer 5 has a laminated structure as shown in FIG. 2, however, it is desired that the insulating layer 5a positioned between the zirconia layer 5b and the cylindrical tube 2 has a thickness of not smaller than 2 $\mu$m.

(Heat-Generating Member 7)

It is desired that the heat-generating member 7 buried in the ceramic layer 5 is a metal selected from the group consisting of platinum, rhodium, palladium and ruthenium, or a an alloy of these metals, and is, particularly, a metal or an alloy having a melting point higher than the firing temperature of the ceramic layer 5 from the standpoint of co-firing with the ceramic layer 5.

The heat-generating member 7 is buried near the measuring electrode 4 or, concretely speaking, around the opening portion 6. When the ceramic layer 5 is constituted by the insulating layer 5a and the zirconia layer 5b as shown in FIG. 2, further, the heat-generating member 7 may be buried in the insulating layer 5a, in the zirconia layer 5b, or may be buried in the boundary portion between the insulating layer 5a and the zirconia layer 5b.

(Electrodes 3, 4 and Opening Portion 6)

As the reference electrode 3 and measuring electrode 4 formed on the surfaces of the cylindrical tube 2, there is used a good conductor metal selected from the group consisting of platinum, rhodium, palladium, ruthenium and gold, or an alloy containing two or more of them. In order to prevent the growth of metal particles in the electrodes during the operation of the sensor and to increase the contact (so-called three-phase interfacial contact) among the metal particles, solid electrolyte and gas that determine the sensor response, furthermore, the ceramic solid electrolytic component for forming the cylindrical tube may be mixed at a ratio of 1 to 50% by volume and, particularly, at a ratio of 10 to 30% by volume in the electrode.

An opening portion 6 is formed in the ceramic layer 5 permitting the measuring electrode 4 to be partly or entirely exposed. That is, the gas to be measured such as exhaust gas is introduced to the measuring electrode 4 through the opening portion 6. Therefore, the portion where the opening 6 is formed serves as a sensing portion of the oxygen sensor device 1. There is no particular limitation on the shape of the opening portion 6 so far as it enables the gas to be measured to be brought in contact in sufficient amounts with the measuring electrode 4. For example, the opening portion 6 may have a vertically elongated rectangular shape as shown in FIG. 1a, or may have a circular shape or an elliptic shape.

Figure 3A:
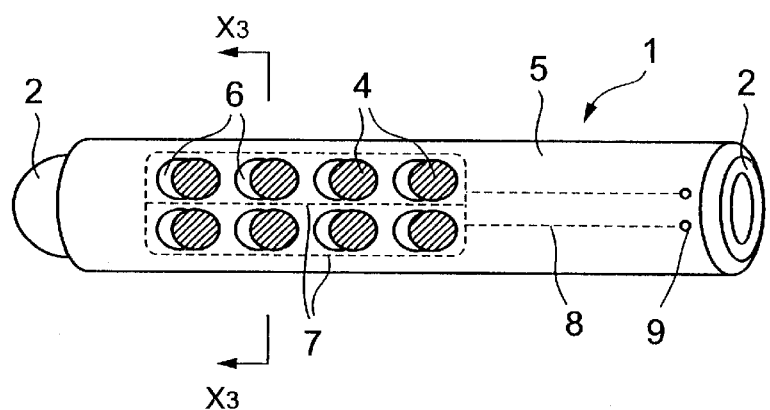
FIG. 3a is a perspective view schematically illustrating the oxygen sensor device having many openings formed in the ceramic layer 5 incorporating the heat-generating member.
Figure 3B:
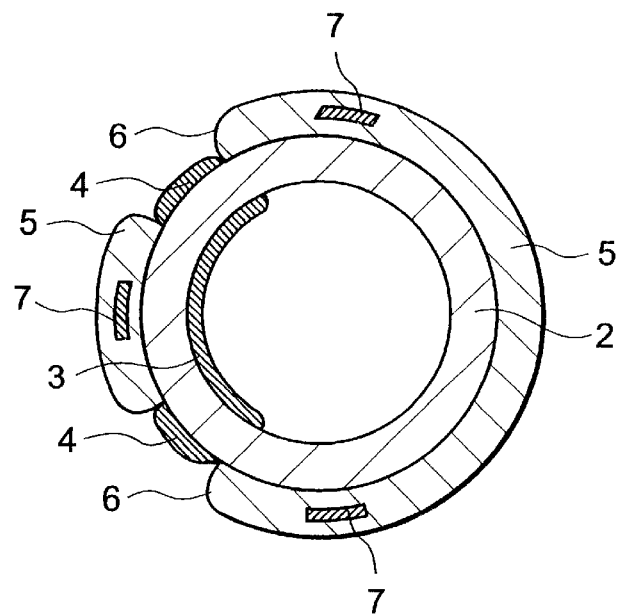

In FIGS. 1a and 1b, the opening portion 6 is formed in a number of one, but it is allowable to form the opening portions 6 in many number, as a matter of course. FIGS. 3a and 3b illustrate an oxygen sensor device having many opening portions 6. FIG. 3a is a perspective view of the oxygen sensor device, and FIG. 3b is a lateral sectional view of FIG. 3a (X3—X3 cross section). In FIGS. 3a and 3b, many opening portions 6 are formed in the ceramic layer 5 incorporating the heat-generating member therein, and the measuring electrodes 4 are exposed through the opening portions 6. The heat-generating member 7 is buried near the opening portions 5. Upon forming many opening portions 6, the sensing portion possesses an increased area to enhance the sensing accuracy.

Further, the reference electrode 3 and the measuring electrodes 4 are so formed that the measuring electrodes 4 exposed through the opening portions 6 are opposed to the reference electrode 3. In the example shown in FIGS. 1a and 1b, the measuring electrode 4 is formed in the opening portion 6 only, and the reference electrode 3 is formed so as to be opposed to the measuring electrode 4. However, it is also allowable to form the measuring electrode 4 of a large area on the outer surface of the cylindrical tube 2, so that the measuring electrode 4 is partly exposed in the opening portion 6, or the reference electrode 3 may be formed on the whole inner surface of the cylindrical tube 2 and the measuring electrode 4 exposed in the opening portion 6 may be opposed to the reference electrode 3.

Figure 4:
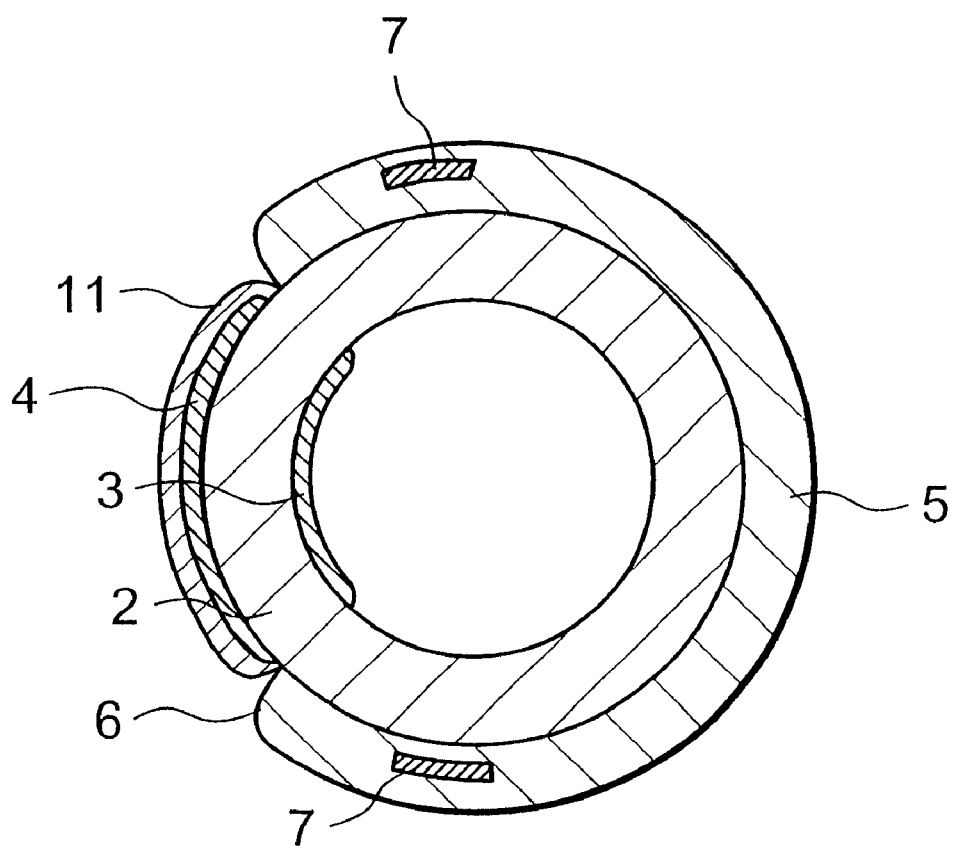
FIG. 4 is a sectional view schematically illustrating the oxygen sensor device in which a porous ceramic layer is formed on the surface of a measuring electrode.

In the present invention, a porous ceramic layer may be formed on the surface of he measuring electrode 4. Referring, for example, to FIG. 4 which is a sectional view illustrating a major portion on an enlarged scale, a porous ceramic layer 11 is formed on the surface of the measuring electrode 4 exposed through the opening portion 6 in the ceramic layer 5 in order to prevent the measuring electrode 4 from being contaminated with the exhaust gas and to avoid a drop in the output voltage caused by the contamination on the measuring electrode 4. The porous ceramic layer 11 can generally be formed by using zirconia, alumina, magnesia or spinel.

When the oxygen sensor device 1 of the invention having the above-mentioned structure is used as a stoichiometric air-fuel sensor ($\lambda$ sensor), it is desired that the open porosity of the porous ceramic layer 11 is within a range of from 10 to 40%. Further, when the oxygen sensor device 1 is used as a wide-range air-fuel ratio sensor device (AF sensor), the porous ceramic layer 11 works as a gas diffusion rate-determining layer. In this case, therefore, it is desired that the open porosity of the porous ceramic layer 11 lies within a range of from 5 to 30%.

It is desired that the porous ceramic layer 11 has a thickness of, generally, from 10 to 200 $\mu$m and, particularly, from 50 to 150 $\mu$m though it may vary depending upon the open porosity thereof.

Figure 5:
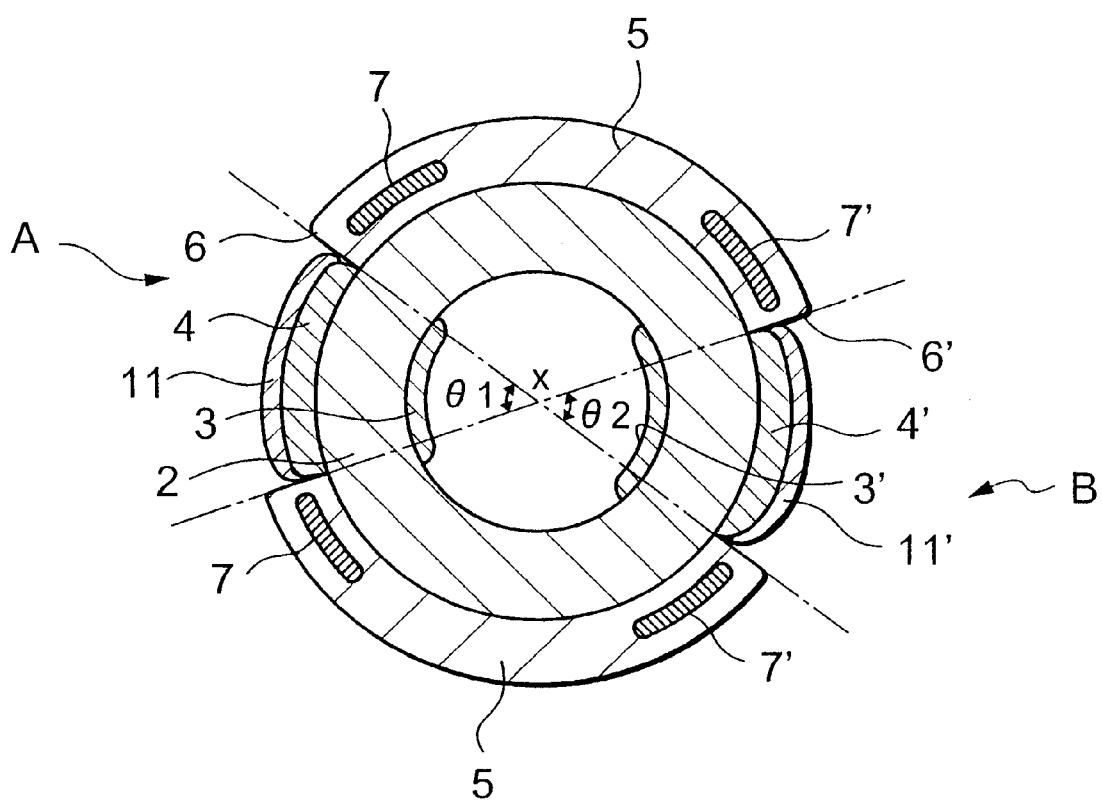
FIG. 5 is a lateral sectional view of the oxygen sensor device in which the two sensing portions are formed facing each other.

As described already, the accuracy of the sensor can be enhanced by forming many opening portions 6 (see FIGS. 3a and 3b). Here, when viewed on a lateral cross section of the oxygen sensor device 1, by forming the two sensing portions in a manner of being opposed to each other with the center of the cylindrical tube 2 sandwiched therebetween the thermal shock resistance of the sensor device 1 can be markedly improved. FIG. 5 is a lateral sectional view of this sensor device 1.

In this oxygen sensor device 1 as will be obvious from FIG. 5, two sensing portions A and B are formed facing each other with the center X of the cylindrical tube 2 sandwiched therebetween. That is, in the sensing portion A, a measuring electrode 4 exposed through an opening portion 6 in the ceramic layer 5 is formed on the outer surface of the cylindrical tube 2, a reference electrode 3 is formed on the inner surface of the cylindrical tube 2 being opposed to the measuring electrode 4, and a porous ceramic layer 11 is formed on the surface of the measuring electrode 4. Further, a heat-generating member 7 is buried surrounding the opening portion 6. In the sensing portion B, on the other hand, an opening portion 6' is formed so as to face the opening portion 6 in the sensing portion A, a measuring electrode 4' exposed through the opening portion 6' is formed on the outer surface of the cylindrical tube 2 like in the sensing portion A, a reference electrode 3' is formed on the inner surface of the cylindrical tube 2 being opposed to the measuring electrode 4', and a porous ceramic layer 11' is formed on the measuring electrode 4'. Further, a heat-generating member 7' is buried surrounding the opening portion 6'.

In general, when the sensing portion (opening portion) is formed in a number of only one as viewed on a lateral cross section, the surrounding of the opening portion 6 is quickly heated by the above-mentioned heat-generating member 7 and, as a result, the thermal stress concentrates surrounding the opening portion 6 often resulting in the development of cracks along the opening portion 6. By forming two sensing portions A and B at opposing positions on the outer surface of the cylindrical tube 2 as shown in FIG. 5, however, the thermal stress generated in the sensing portions is canceled and relaxed by each other to effectively suppress the occurrence of cracks. That is, the oxygen sensor device 1 of the structure shown in FIG. 5 has very excellent thermal shock resistance.

In the oxygen sensor device 1 of FIG. 5, it is desired that the opening portion 6 in the sensing portion A has a shape same as that of the opening portion 6' in the sensing portion B, but the shapes may be different from each other. When the shape of the opening portion 6 is different from the shape of the opening portion 6', it is desired that the area of the opening portion 6' is from 50% to 150% of the area of the opening portion 6. This is because when these two areas are greatly different from each other, the stress generated around the opening portions 6, 6' is not effectively canceled. Further, the opening portions 6 and 6' may be formed in many number being arranged in the axial direction (lengthwise direction) of the cylindrical tube 2 maintaining a predetermined distance as shown in FIG. 3.

The expanding angles $\theta 1$ and $\theta 2$ of the opening portion 6 in the sensing portion A and of the opening portion 6' in the sensing portion B from the canter X of the cylindrical tube are preferably within a range of from 30 to 90 degrees and, particularly, from 40 to 90 degrees. When the expanding angles $\theta 1$ and $\theta 2$ are too small, stress concentrates to a conspicuous degree around the openings 6 and 6', and cracks may develop. When the expanding angles $\theta 1$ and $\theta 2$ are too large, on the other hand, the heating efficiency of the heat-generating members 7 decreases, and the capacity of the heaters must be increased.

In order that the thermal stress generated around the opening portion 6 is effectively canceled by the thermal stress generated around the opening portion 6', it is most desired that the lines connecting the centers of the opening portions 6, 6' to the center X of the cylindrical tube 2 are on a straight lines. However, there arouses no particular problem if the deviating angle of these lines is not larger than 10 degrees.

(Other Embodiments of the Oxygen Sensor Device)

The above-mentioned oxygen sensor device 1 of the present invention can be designed in various other ways.

For example, the opening portion 6 in the ceramic layer 5 through which the measuring electrode 4 is exposed is covered with a solid electrolyte layer having an oxygen ion conducting property, the electrodes are formed on the outer surface of the solid electrolyte layer and on the inner surface thereof (on the side of the opening portion 6) to markedly improve the thermal shock resistance of the oxygen sensor device 1 and to quickly raise the temperature in order to further shorten the time (activating time) until the activating temperature is reached.

Figure 6A:
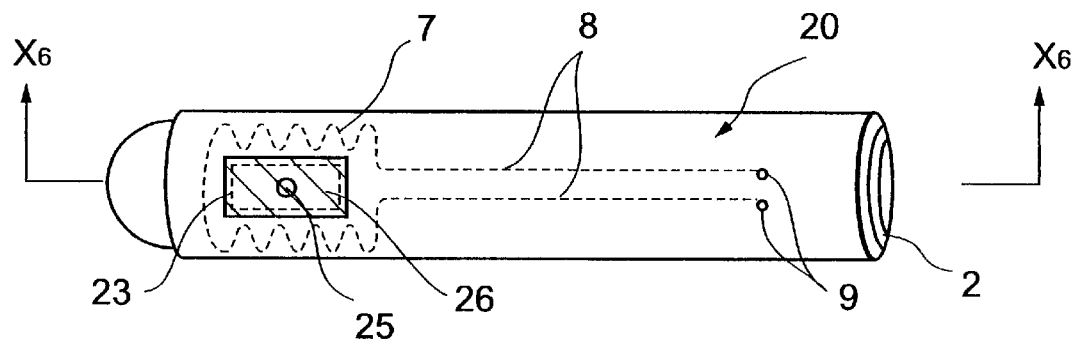
FIG. 6a is a perspective view schematically illustrating another oxygen sensor device of the present invention.
Figure 6B:
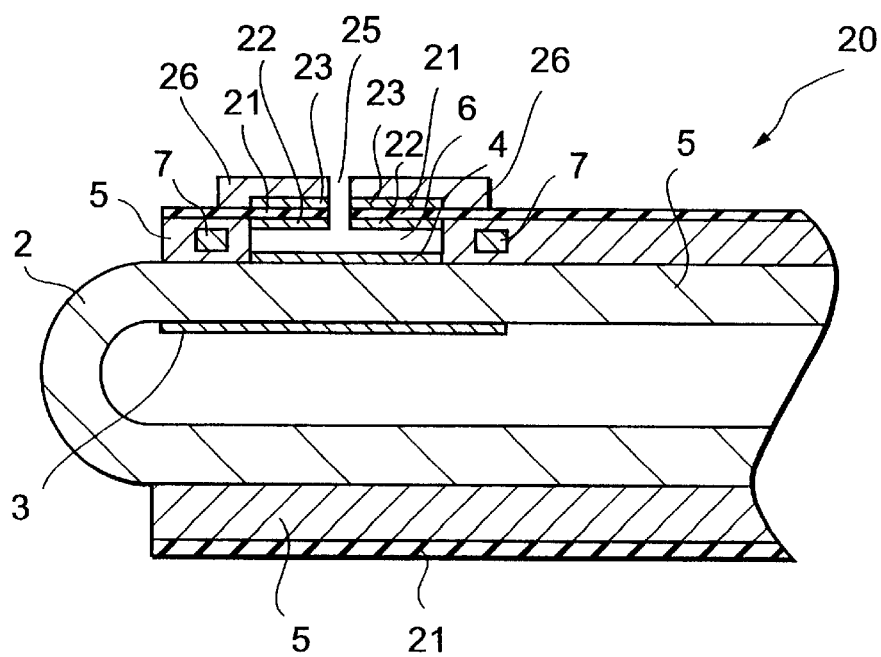

FIG. 6a is a sectional view schematically illustrating the above oxygen sensor device, and FIG. 6b is a vertical sectional view thereof (X6—X6 cross section).

In FIGS. 6a and 6b, the structure of the oxygen sensor device 20 is basically the same as that of the oxygen sensor device 1 shown in FIGS. 1a and 1b. That is, the oxygen sensor device 20, too, is provided with a cylindrical tube 2 of a ceramic solid electrolyte having an oxygen ion conducting property, and includes a reference electrode 3, a measuring electrode 4, a ceramic layer 5 incorporating a heat-generating member, an opening portion 6 and a heat-generating member 7 quite in the same manner as the oxygen sensor device 1. That is, the heat-generating member 7 is connected to terminal electrodes 9 through lead electrodes 8, and an electric current is supplied to the heat-generating member 7 through them to quickly heat the sensing portion up to a predetermined temperature.

In the oxygen sensor device 20 of FIGS. 6a and 6b, a solid electrolyte layer 21 is laminated on the ceramic layer 5 incorporating a heat-generating member in a manner to close the opening portion 6, and an inner electrode 22 and an outer electrode 23 are formed on the inner surface and on the outer surface of the solid electrolyte 21 positioned on the opening portion 6. As will be obvious from FIG. 6b, in particular, the inner electrode 22 and the outer electrode 23 are opposed to each other with the solid electrolyte layer 21 sandwiched therebetween.

The solid electrolyte layer 21 is a ceramic solid electrolyte having an oxygen ion conducting property quite like the cylindrical tube 2, and a gas diffusion hole 25 is formed on the opening portion 6 in the solid electrolyte layer 21 to introduce a gas to be measured into space in the opening portion 6. That is, a sensing cell is formed by a first pair of electrodes, i.e., reference electrode 3 and measuring electrode 4 with the solid electrolytic circular tube 2 sandwiched therebetween, thereby to measure a limit current value due to a difference in the oxygen concentration between the reference gas and the exhaust gas (being measured). Further, a pumping cell is formed by a second pair of electrodes, i.e., inner electrode 22 and outer electrode 23 with the solid electrolyte layer 21 sandwiched therebetween. The pumping cell controls the concentration of oxygen to a predetermined value in space in the opening portion 6 closed by the solid electrolyte layer 21.

In the thus constituted oxygen sensor device 20, the heat-generating member 7 is buried to surround the opening portion 6 and, besides, radiation of heat from the opening portion 6 is suppressed by the solid electrolyte layer 21. Accordingly, the first pair of electrodes (reference electrode 3 and measuring electrode 4) forming the sensing cell, and the second pair of electrodes (inner electrode 22 and outer electrode 23) forming the pumping cell are quickly heated to effectively shorten the activating time.

Further, the solid electrolyte layer 21 on the ceramic layer 5 is formed of the ceramic material same as that of the cylindrical tube 2. Therefore, the thermal stress caused by a difference in the thermal expansion or by a difference in the contraction after firing between the ceramic layer 5 and the cylindrical tube 2, is relaxed by the solid electrolyte layer 21 enabling the oxygen sensor device 20 to exhibit excellent thermal shock resistance.

In the present invention, it is desired that the solid electrolyte layer 21 has a thickness of from 100 to 350 $\mu$m and, particularly, from 150 to 300 $\mu$m. When the thickness of the solid electrolyte layer 21 is smaller than the above range, the solid electrolyte layer 21 fails to exhibit a sufficiently large strength and tends to be broken. On the other hand, when the thickness of the solid electrolyte layer 21 is larger than the above range, the oxygen ion conducting property decreases and the sensor device 21 exhibits poor gas response.

Referring to FIG. 6b, the oxygen sensor device 20 has an electrode protection layer 26 formed on the outer surface of the outer electrode 23. The electrode protection layer 26 is formed of the same ceramic material as the porous ceramic layer 11 shown in FIG. 4, and, like the porous ceramic material, prevents the surface of the outer electrode 23 from being contaminated by the exhaust gas. Though not shown in FIG. 6b, the surface of the inner electrode 22 and the surface of the measuring electrode 4 may be similarly provided with the electrode protection layer 26 (porous ceramic layer 11).

It is desired that the diffusing hole 25 formed in the solid electrolyte layer 21 has a size of, generally, from 100 to 500 $\mu$m. Further, the diffusing holes 25 may be formed in many numbers. The diffusing holes 25 are formed in the solid electrolyte layer 21. However, the diffusing holes 25 may be formed at any positions so far as the exhaust gas is introduced into the opening portion 6.

Figure 7:
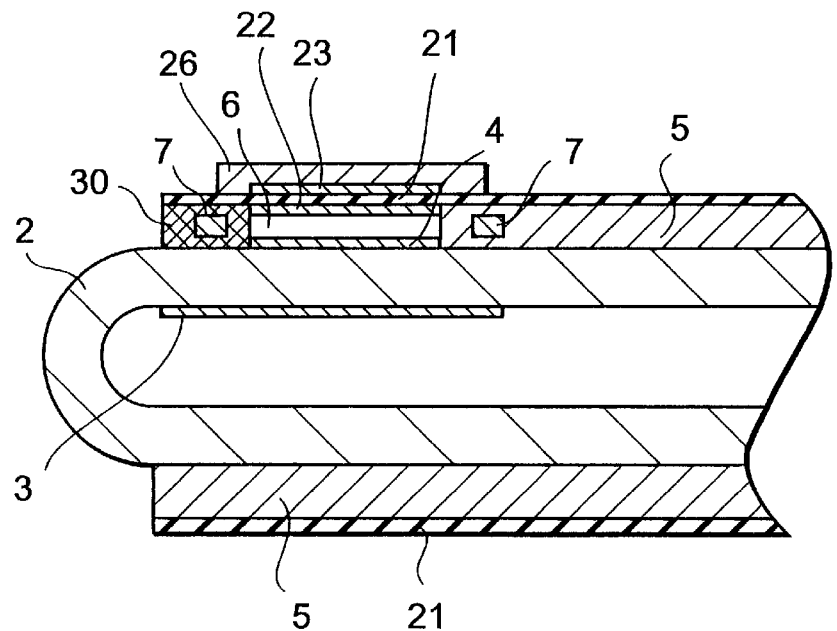
FIG. 7 is a sectional view of the oxygen sensor device of FIG. 6a, in which porous blocks are formed surrounding the opening portions, and pores in the blocks are utilized as diffusing holes instead of forming diffusing holes in the solid electrolyte layer that closes the opening portions.

In FIG. 6b, for example, the diffusing hole 25 may be formed in the ceramic layer 5 positioned on the left side of the opening portion 6 so as to extend toward the side of closed portion of the cylindrical tube 2 along the outer surface of the cylindrical tube 2, in order to introduce the exhaust gas into space in the opening portion 6. Referring to FIG. 7, further, a porous ceramic block 30 may be provided on the left side of the opening portion 6. That is, the block 30 is formed of the same porous ceramic material as the above-mentioned porous ceramic layer 11, and pores possessed by the ceramic material can be used as diffusing holes 25.

In the oxygen sensor device 20, further, space in the opening portion 6 closed by the solid electrolyte layer 21 may be provided with a shielding wall of the same porous material as the porous ceramic layer 11. That is, referring to FIG. 8, a porous cylinder 31 formed of the porous ceramic material for protecting the electrode is arranged just under the diffusing hole 25 in space in the opening portion 6. Upon arranging the cylinder 31, the exhaust gas introduced into the opening portion 6 through the diffusing hole 25 is prevented from coming into direct contact with the surfaces of the measuring electrode 4 and of the inner electrode 22; i.e., the electrodes 4 and 22 are effectively prevented from being contaminated.

Figure 8:
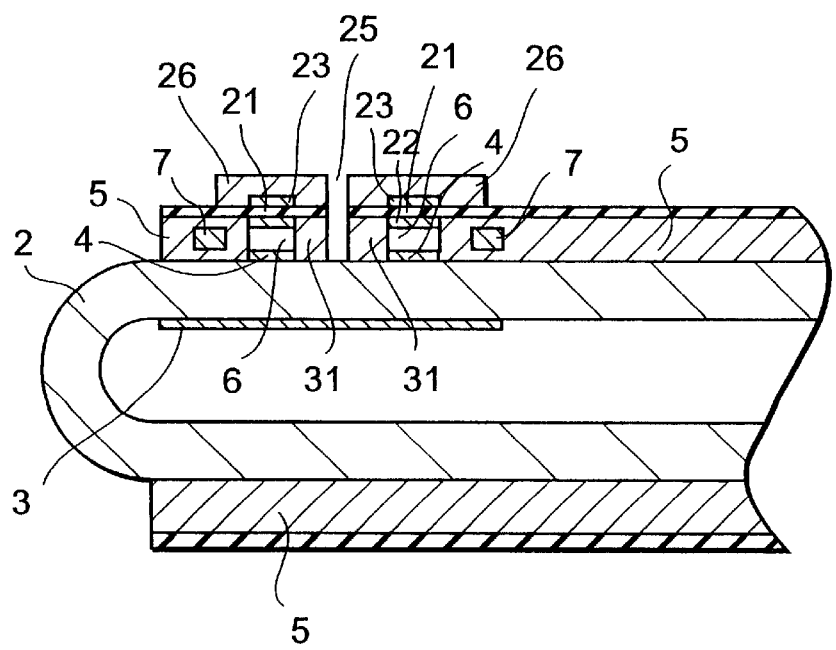
FIG. 8 is a sectional view of the oxygen sensor device of FIG. 6a, in which spaces in the opening portions 6 closed by the solid electrolyte layer are provided with porous cylinders to protect the electrode.

In the example of FIG. 8, the porous cylinder 31 is arranged in a portion of space in the opening portion 6 closed by the solid electrolyte layer 21. However, the entire space in the opening portion 6 may be filled with the porous ceramic material. With space in the opening portion 6 being filled with the porous ceramic material, the solid electrolyte layer 21 positioned on the upper part is reinforced to relax mechanical shock such as thermal shock and to further increase the thermal shock resistance of the sensor device 21. As described earlier, the porous ceramic material filling the opening portion 6 is the one forming the porous ceramic layer 11, such as zirconia, alumina, spinel or forsterite. From the standpoint of coefficient of thermal expansion, however, it is desired to use zirconia or spinel.

In filling the opening portion 6 with the porous ceramic material as described above, further, it is desired that the void volume in the opening portion 6 (corresponds to porous volume of the porous ceramic material filled therein) is within a range of from $20 \times 10^{-3}$ to $100 \times 10^{-3}$ mm$^3$ and, particularly, from $40 \times 10^{-3}$ to $80 \times 10^{-3}$ mm$^3$ (the void volume is measured by the mercury intrusion porosity method. When the void volume is smaller than the above range, the pumping current of the second pair of electrodes (inner electrode 22 and outer electrode 23) becomes small, arousing a problem in the measuring accuracy and making it difficult to detect the air-fuel ratio over a wide range. When the void volume is larger than the above range, on the other hand, the solid electrolyte layer 21 may be broken due to Joule heat generated by the inner electrode 22 and the outer electrode 23.

As described above by way of various examples, the oxygen sensor device incorporating a heater of the invention has a cylindrical shape as a whole and is so constructed that thermal or mechanical stress concentrates little, and exhibits very excellent strength, thermal shock resistance and durability compared with the oxygen sensor device incorporating a heater of the type of a flat plate. Further, the heat-generating member in arranged near the electrode, and the sensing portion is heated by being directly heated thereby. Thus, the sensing portion is quickly heated within a very shortened period of time until the activating temperature is reached, and a very excellent sensor response is accomplished.

An will be described below, further, the oxygen sensor device of the invention can be produced by co-firing the cylindrical tube, various electrodes and various ceramic layers through a decreased number of production steps at a decreased cost, offering advantage even from the standpoint of economy.

(Production of Oxygen Sensor Device)

As described above, the oxygen sensor device of the present invention can be produced by the so-called co-firing. The oxygen sensor devices of various structures shown in FIGS. 1 to 8 can be produced according to a process shown in, for example, FIGS. 9a to 9c (first production process) or a process shown in FIGS. 10a to 10d (second production process).

Figure 9A:
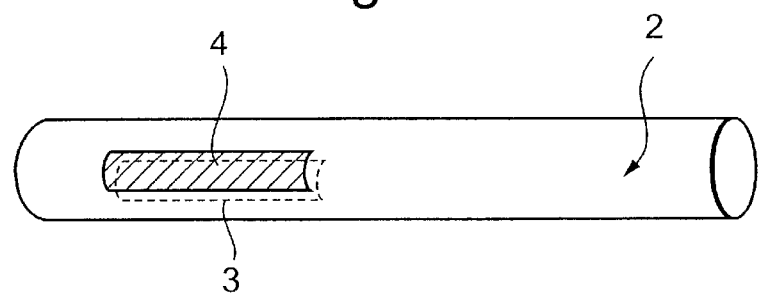
FIGS. 9a to 9c are views illustrating a process for producing the oxygen sensor device of the invention.
Figure 9B:
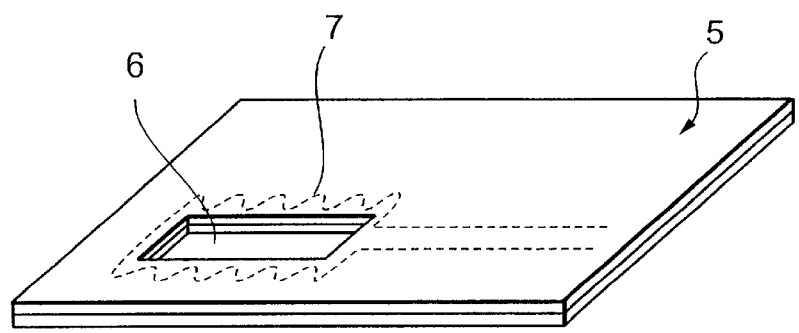
Figure 9C:
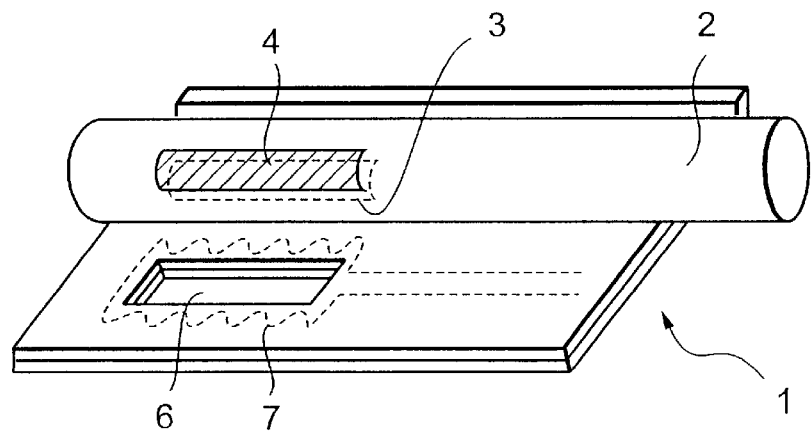

First Production Process:

According to the first production process shown in FIGS. 9a to 9c, a cylindrically molded article 2 (corresponds to the cylindrical tube 2) with its one end closed is formed as shown in FIG. 9a by using a powder of a ceramic solid electrolyte for forming the cylindrical tube. The molding is executed by a known method such as extrusion molding, hydrostatic molding (rubber press) or press molding by using a molding slurry prepared by suitably adding an organic binder for molding to the powder of the ceramic solid electrolyte.

Patterns 3 and 4 of an electrically conducting paste (containing the above-mentioned metal or alloy for forming electrodes) corresponding to the reference electrode 3 and measuring electrode 4 are formed on the inner surface and on the outer surface of the cylindrically molded article 2 by slurry-dipping method, screen-printing method, pad-printing method or roll transfer method. The pattern 3 can also be formed on the inner surface of the cylindrically molded article 2 by filling space in the cylindrically molded article 2 with an electrically conducting paste and, then, discharging the electrically conducting paste. In this case, the pattern 3 of the electrically conducting paste is applied and formed onto the whole inner surface of the cylindrically molded article 2.

Referring next to FIG. 9b, a laminated ceramic green sheet 5 in prepared having an opening portion 6 and a heat-generating member 7 buried near the opening portion 6. The laminated ceramic green sheet 5 corresponds to the above-mentioned ceramic layer 5 containing a heat-generating member, and is prepared by using a ceramic powder for molding the ceramic layer 5.

That is, an organic binder for molding is suitably added to the ceramic powder to prepare a slurry which is, then, formed into a green sheet by a doctor blade method, an extrusion molding method or a press method. It is desired that the green sheet has a thickness of from 50 to 500 $\mu$m and, particularly, from 100 to 300 $\mu$m from the standpoint of handling. Next, to form the above-mentioned heat-generating member 7, an electrically conducting paste containing a metal or an alloy is printed onto the green sheet prepared above relying on the screen-printing method, pad-printing method or roll transfer method. The green sheet without the heat-generating member pattern 7 is laminated on the green sheet that has the heat-generating member pattern 7 to obtain the laminated ceramic green sheet 5. The desired ceramic green sheet 5 can also be obtained even by applying a slurry containing the ceramic power onto the surface of the green sheet having the heat-generating member pattern 7 by the printing method or the transfer method. Further, the opening portion 6 can be formed by punching in the laminated green sheet 5 or in the green sheet of before being laminated.

Referring next to FIG. 9c, the thus obtained laminated green sheet 5 is wound on the surface of the cylindrically molded article 2 prepared in FIG. 9a above and is adhered thereto to prepare a laminated cylinder 1 corresponding to the oxygen sensor device 1. The laminated green sheet 5 is easily adhered and secured by being wound on the cylindrically molded article 2 with an adhesive such as acrylic resin or organic solvent interposed therebetween. Further, the laminated green sheet 5 can be mechanically adhered onto the cylindrically molded article 2 by applying a pressure using a roller or the like.

Upon firing the thus obtained laminated cylinder 1, the cylindrically molded article 2 and the laminated green sheet 5 incorporating a heat-generating member therein are co-fired making it possible to obtain the oxygen sensor device 1 incorporating a heater therein of the present invention. The firing is usually conducted in an inert atmosphere such as of argon gas or in the open air at a temperature of from 1300 to 1700° C. for about 1 to about 10 hours.

Second Production Process:

In the above-mentioned first production process, the conductor pattern 4 (corresponds to the measuring electrode 4) was formed on the outer surface of the cylindrically molded article 2. However, the conductor pattern 4 may be formed in a laminate that is to be wound on the cylindrically molded article 2 as done by the second production process shown in FIGS. 10a to 10d.

Figure 10A:
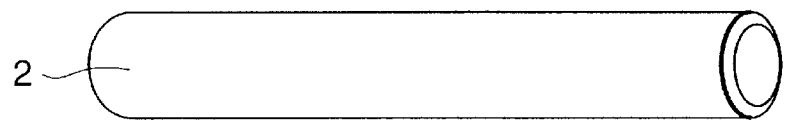
FIGS. 10a to 10d are views illustrating another process for producing the oxygen sensor device of the invention.

In the second production process, first, the cylindrically molded article 2 shown in FIG. 10a is prepared in the same manner as in the first production method, and a conductor pattern (not shown) corresponding to the reference electrode 3 is formed on the inner surface thereof. The conductor pattern is formed by quite the same method as the first production process.

Figure 10B:
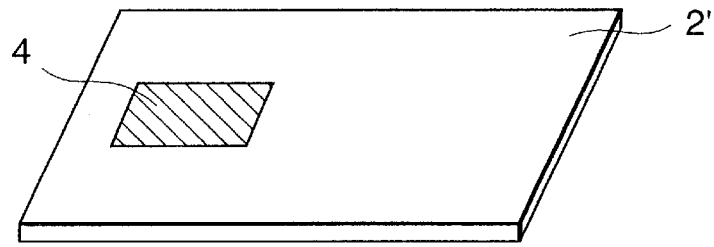

Next, a slurry containing the solid electrolytic ceramic used for forming the cylindrically molded article 2 is formed into a solid electrolytic green sheet 2' shown in FIG. 10b by the doctor blade method, extrusion molding method or press method. It is desired that the green sheet 2' has a thickness of from 50 to 500 μm and, particularly, from 100 to 300 μm from the standpoint of handling the sheet. An electrically conducting paste containing a metal or an alloy for forming an electrode is applied by printing onto a predetermined place on the surface of the solid electrolytic green sheet 2' thereby to form the conductor pattern 4 (corresponds to the measuring electrode 4).

Figure 10C:
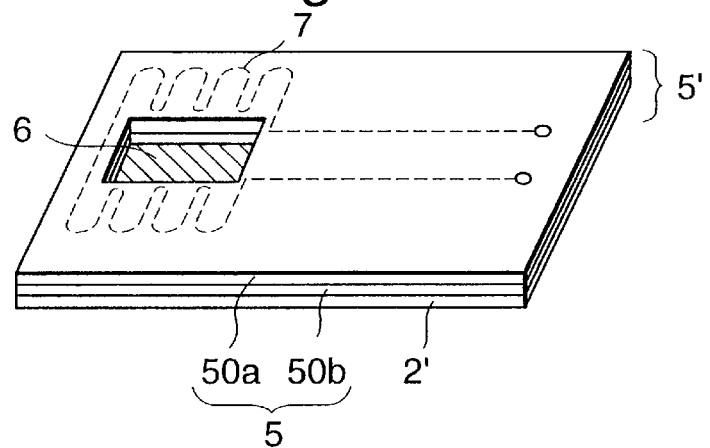

Referring to FIG. 10c, the ceramic laminate 5 incorporating the heat-generating member is laminated on one surface of the solid electrolytic green sheet 2' (on the side where the conductor pattern 4 is formed) thereby to obtain a laminated green sheet 5'. The ceramic laminate 5 incorporating the heat-generating member is quite the same as the one shown in FIG. 9b, and is constituted by two pieces of ceramic green sheets 50a and 50b, having the opening portion 6 formed in a predetermined place and the heat-generating member 7 buried near the opening portion 6. As will be obvious from FIG. 10c, the conductor pattern 4 formed on the surface of the solid electrolytic green sheet 2' is exposed through the opening portion 6.

Figure 10D:
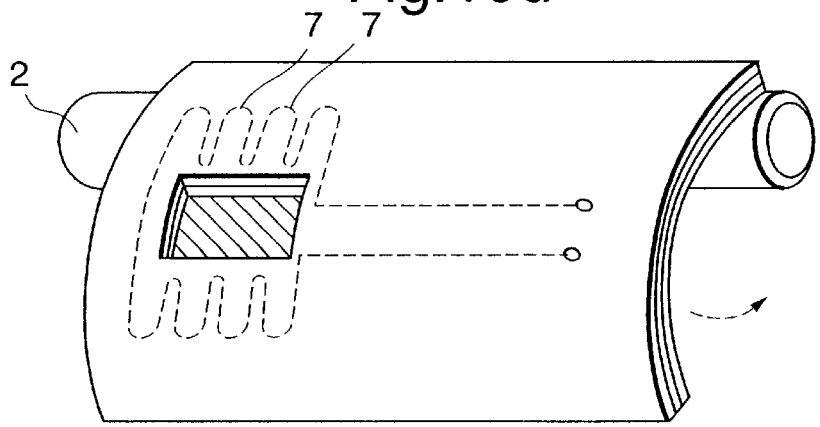

The thus obtained laminated green sheet 5' is wound, as shown in FIG. 10d, on the cylindrically molded article 2 in the same manner as in FIG. 9c and is adhered and secured thereto to form the laminated cylinder 1 which is then fired to obtain a desired oxygen sensor device 1 incorporating a heater therein as contemplated by the invention.

In the above-mentioned first and second production processes, the conductor patterns 3 and 4 for forming the reference electrode 3 and the measuring electrode 4 can be formed on the laminated cylinder 1 of before being fired. That is, the conductor pattern 4 is formed by printing the electrically conducting paste for forming electrode on a portion where the opening portion 6 is formed in the laminated cylinder 1 by the screen printing, pad printing or roll transfer, followed by firing. Or, the electrically conducting paste is applied into space in the laminated cylinder 1 (cylindrically molded article 2) by the slurry-dipping method or the like method to form the conductor pattern 3. Further, after the laminated cylinder 1 is fired, the electrically conducting paste is printed onto predetermined positions and is fired to form the reference electrode 3 and the measuring electrode 4. Or, these electrodes may be formed by a thin-film method such as sputtering method or plating method.

The oxygen sensor device 1 of the structure shown in FIGS. 1a and 1b can be easily produced by utilizing the above-mentioned first or second production process. By suitably adjusting the shape and number of the opening portions 6 and the position of the conductor pattern 4, further, the oxygen sensor devices 1 of the structures shown in FIGS. 3a, 3b and 5 can be produced. Further, when the ceramic layer 5 incorporating the heat-generating member is constituted by the insulating ceramic layer 5a and the zirconia layer 5b as shown in FIG. 2, the ceramic laminate 5 incorporating the heat-generating member produced by the first or second production process may have a layer structure as shown in FIG. 2.

To produce the oxygen sensor device 1 having the porous ceramic layer 11 formed on the surface of the measuring electrode 4 as shown in FIG. 4, further, the laminated cylinder 1 is fired, a slurry containing the porous ceramic powder is applied by printing onto the surface of the measuring electrode 4 by the sol-gel method, slurry-dipping method or printing method, followed by firing. The porous ceramic layer 11 may be formed by applying the porous ceramic by the sputtering method of plasma melt-injection method. In preparing the laminated cylinder 1, further, a slurry containing the porous powder may be applied onto the surface of the conductor pattern 4 that becomes the measuring electrode 4 and may be co-fired with the laminated cylinder 1 to form the porous layer 11.

In producing the oxygen sensor device 20 of the structure shown in FIG. 6a according to the first and second production methods, further, a ceramic sheet (having conductor patterns corresponding to the inner electrode 22 and the outer electrode 23) for forming the solid electrolyte layer 21 may be laminated on the laminated ceramic green sheet 5 or 5' incorporating the heat-generating member that is to be wound on the cylindrically molded article 2. The process for producing such a ceramic sheet is shown in FIGS. 11a to 11b.

That is, referring to FIG. 11a, a ceramic green sheet 21 (corresponds to the solid electrolyte layer 21) is formed as shown in FIG. 11a by using a slurry containing the same solid electrolytic ceramic as the one used for forming the cylindrical tube 2. The green sheet 21 is prepared by the same method as the one for preparing the green sheet in the first or second production process, and has the same thickness. The green sheet 21 has, on the surface thereof, a conductor pattern 22 corresponding to the inner electrode 22 and a conductor pattern 23 corresponding to the outer electrode 23. The conductor patterns 22 and 23 are formed by the same method as the one for forming the conductor patterns 3 and 4.

Referring to FIG. 11b, the laminated ceramic green sheet 5 incorporating the heat-generating member is laminated on the ceramic green sheet 21 in a manner that the conductor pattern 22 (corresponding to the inner electrode 22) is positioned in the opening portion 6 thereby to prepare a laminated sheet A that is to be wound on the cylindrically molded article 2. The laminated sheet A is wound on the cylindrically molded article 2 followed by firing to obtain the oxygen sensor device 20 of the structure shown in FIGS. 6a and 6b. The diffusing hole 25 can be formed in any step using a micro-drill or the like means after the laminated sheet A is prepared. It is, however, desired that the diffusing hole 25 is formed in a step of before being fired from the standpoint of operability and yield.

It is further allowable to prepare the laminated sheet A by applying a slurry containing a ceramic powder for forming the ceramic layer 5 on the surface of the ceramic green sheet 21 on a side on where the conductor pattern 22 is formed, forming a conductor pattern corresponding to the heat-generating member on the slurry layer, and applying thereon a slurry containing the ceramic powder for forming the ceramic layer 5. To form the electrode protection layer 26 on the outer electrode 23, further, a slurry containing the porous ceramic should be applied in advance onto the conductor pattern 23 of the ceramic green sheet 21.

In producing the oxygen sensor device 20 having the porous block 30 formed surrounding the opening portion 6 as shown in FIG. 7 or in producing the oxygen sensor device 20 having a porous cylinder 31 formed in space in the opening portion 6 as shown in FIG. 8, furthermore, a ceramic slurry should be applied to a predetermined portion of the green sheet 21 to form the porous block 30 or the porous cylinder 31. In producing the oxygen sensor device in which the opening portion 6 closed by the solid electrolyte layer 21 is filled with the porous ceramic, further, a portion corresponding to the opening portion 6 in the laminated sheet A should be filled with a slurry containing the porous ceramic.

Figure 12:
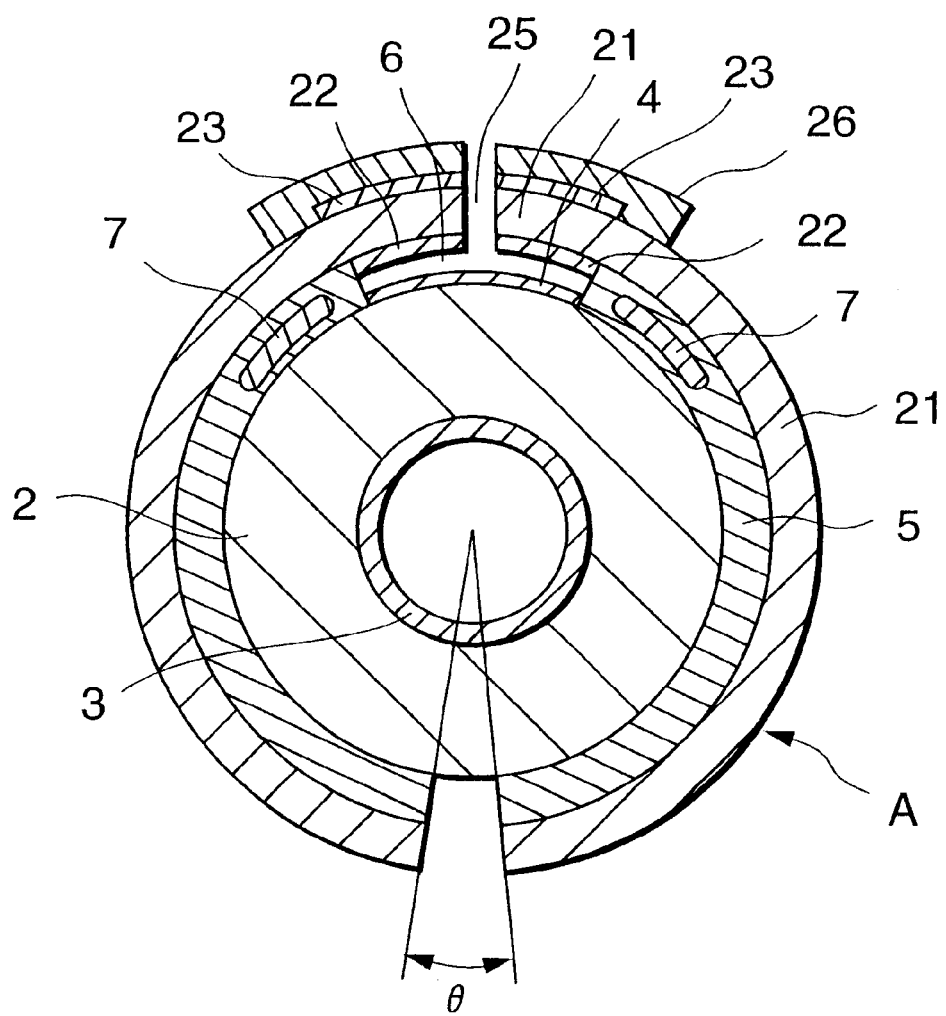
FIG. 12 is a sectional view illustrating a positional relationship of both ends of the laminated sheet wound on the cylindrically molded article (cylindrical tube)

In the present invention, further, the ends of the laminated ceramic green sheet 5 or the laminated sheet 5 wounded on the cylindrically molded article 2 may be overlapped one upon the other by taking the shrinkage at the time of firing into consideration, or may be separated away from each other so as to form a predetermined gap between the two. From the standpoint of thermal shock resistance, however, it is desired that the two ends are separated away from each other, i.e., are not overlapped one upon the other. Referring, for example, to FIG. 12 which is a sectional view illustrating the oxygen sensor device 20 of FIGS. 6a and 6b, it is desired that both ends of the laminated sheet A wound on the cylindrically molded article 2 (cylindrical tube 2) is so separated that the expansion angle $\theta$ is from 5 to 50 degrees and, particularly, from 10 to 25 degrees with the cylindrical tube 2 as a center. When the expansion angle $\theta$ is smaller than the above range, both ends of the laminated sheet A may be partly overlapped to deteriorate the yield of the obtained devices. When the expansion angle $\theta$ is larger than the above range, on the other hand, the obtained device may be deformed in an elliptic shape during the firing to lose the thermal shock resistance.

EXAMPLES (Example 1)

There were provided a spinel powder, an alumina powder, a zirconia powder containing 5 mol % of $Y_2O_3$ and a platinum powder that have been placed in the market.

First, a slurry was prepared by adding a polyvinyl alcohol solution to the zirconia powder containing 5 mol % of $Y_2O_3$, and was extrusion-molded to obtain a cylindrically molded article having an outer diameter of about 5 mm, an inner diameter of 3 mm and is closed at its one end.

Further, the polyvinyl alcohol solution was added to the spinel powder to prepare a slurry which was the formed into a green sheet of about 200 $\mu$m thick. An opening portion was formed in the green sheet by punching, an electrically conducting paste containing the platinum powder was screen-printed in a pattern of a heat-generating member near the opening portion, and the slurry containing the spinel powder was applied thereon to prepare a laminated ceramic sheet in which the heat-generating member was buried.

An acrylic resin was applied as an adhesive onto the surface of the cylindrically molded article, and the laminated ceramic sheet was wound thereon to prepare a laminated cylinder.

The laminated cylinder was fired in the open air at 1500° C. for 2 hours. Then, a porous reference electrode and a porous measuring electrode (2 $\mu$m thick) of platinum were formed by nonelectrolytic plating on the surface in the opening portion of the cylindrical tube and on the whole inner surface of the cylindrical tube.

Thereafter, a ceramic protection layer of spinel having a porosity of 30% was formed on the surface of the measuring electrode in the opening portion by plasma melt-injection maintaining a thickness of 200 $\mu$m to prepare the stoichiometric air-fuel ratio sensor shown in FIGS. 1a and 1b, and to evaluate it.

Figure 13:
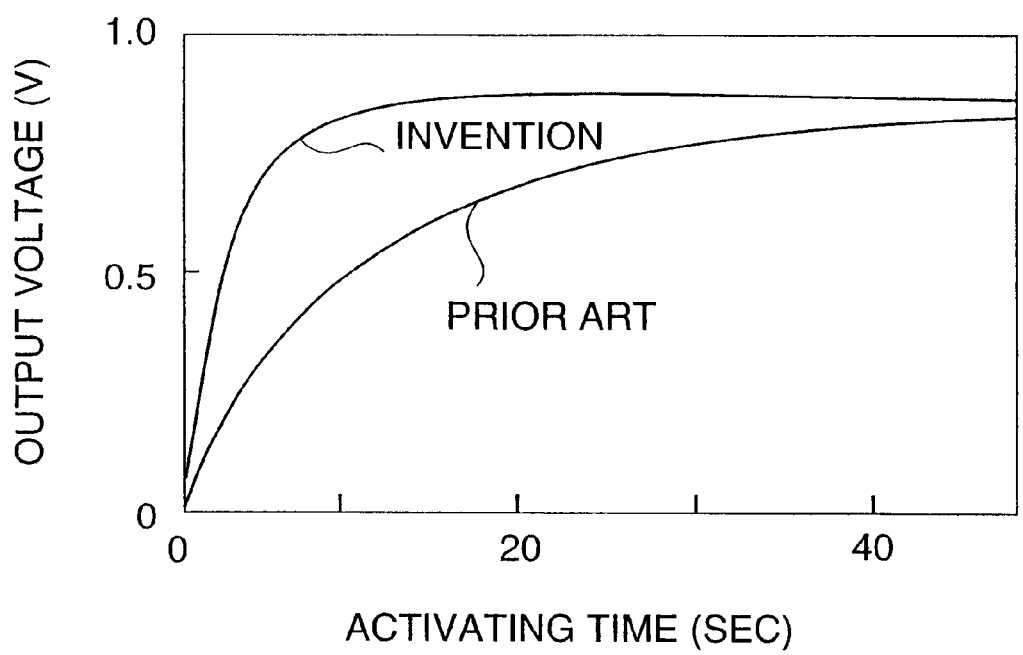
FIG. 13 is a diagram illustrating the measured activating times of the sensor device produced in Example 1 while feeding a mixture gas at a temperature of 700° C. such that an excess air ratio is 0.95.

The activating time the sensor device was measured when the air was supplied to the reference electrode and HC, CO, $H_2$ and air ($O_2$) were supplied to the measuring electrode at 700° C. in a manner that the excess air ratio was 0.95. The results were as shown in FIG. 13. For comparison, a commercially available cup-shaped oxygen sensor incorporating a heater in the cylindrical tube was also measured for the activating time was reached.

It will be understood from the results of FIG. 13 that the commercially available cup-shaped oxygen sensor device requires a time of about 50 seconds before it is activated whereas the oxygen sensor device incorporating the heater therein of the present invention works in 15 seconds.

Figure 14:
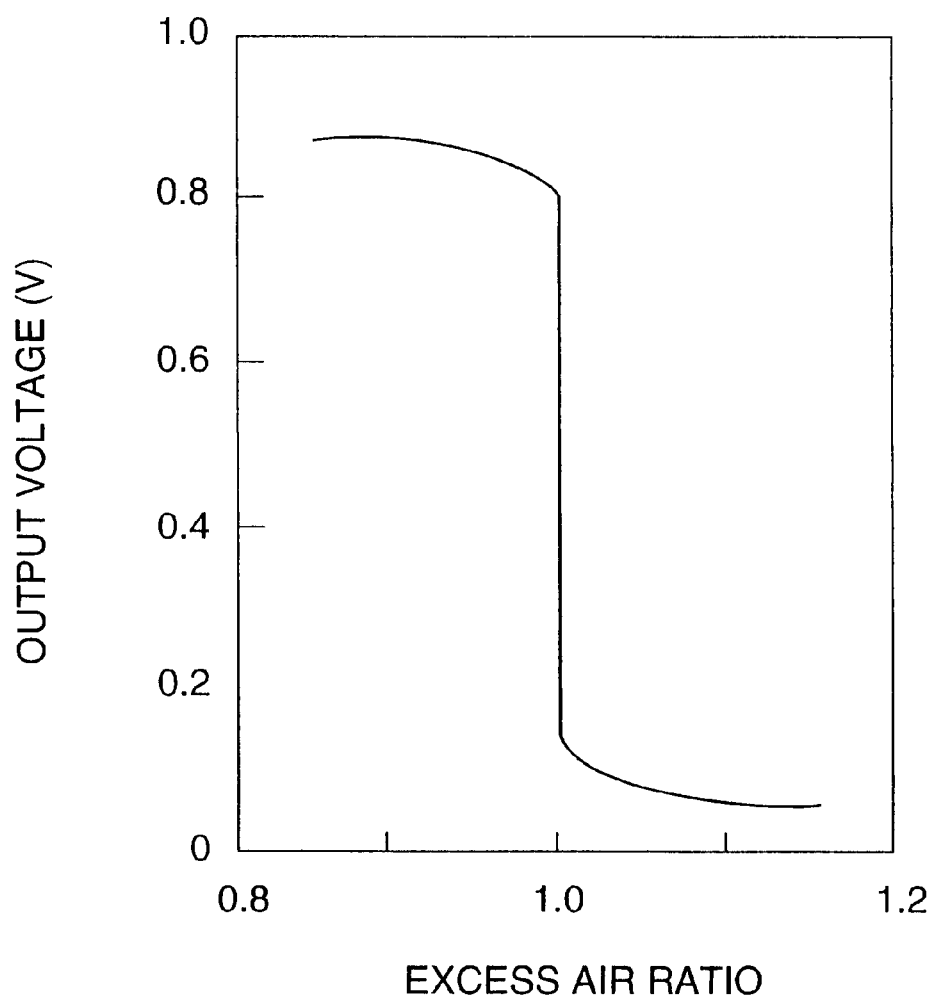
FIG. 14 is a diagram illustrating a relationship between the output voltage of the sensor device of Example 1 at 700° C. an excess air ratio.

FIG. 14 illustrates a relationship between the output voltage and the excess air ratio of the oxygen sensor device incorporating the heater of the present invention at 700° C. It will be understood from FIG. 14 that the output voltage sharply changes when the excess air ratio is near 1. It is thus obvious that the oxygen sensor device of the invention exhibits a function which is sufficient for controlling the ratio of mixing the fuel and air near the stoichiometric air-fuel ratio, and is very useful as a stoichiometric air-fuel ratio sensor.

Figure 19:
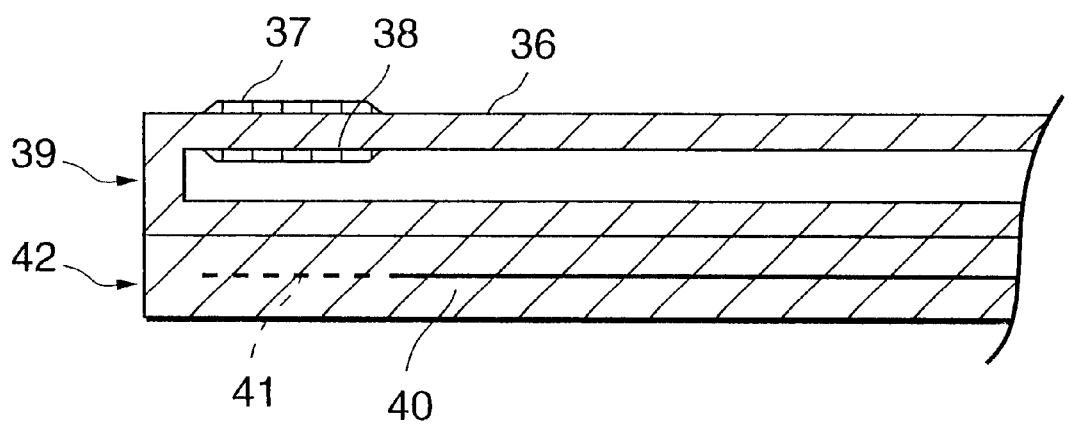
FIG. 19 is a perspective view schematically illustrating a widely known flat-plate type oxygen sensor incorporating a heater.

The thus produced oxygen sensor devices incorporating the heater in a number of twenty were examined for their reliability by subjecting them to the temperature cycle testing. That is, the temperature was elevated from room temperature up to 700° C. in 20 seconds and was then quickly cooled down to room temperature, forming one cycle. After this cycle was repeated 100,000 times, an increase in the resistance of the heater buried in the sensor was measured with respect to the initial value. Further, the flat-plate type oxygen sensor device incorporating the heater of a structure, shown in FIG. 19, constituted by using the flat-plate type oxygen sensor of the zirconia solid electrolyte and an insulating substrate (with a platinum heat-generating member buried therein) of alumina ceramics, was examined for its reliability quite in the same manner.

In the case of the flat-plate type oxygen sensor device incorporating the heater, an average increase in the resistance of the heater was 3.5%. In the case of the oxygen sensor device of the present invention, on the other hand, an average increase in the resistance was 0.4%, proving excellent heat cycle resistance.

(Example 2)

A wide-range air-fuel sensor device was prepared in the same manner as in Example 1 but applying the zirconia powder onto the surface of the measuring electrode by the slurry-dipping method instead of melt-injecting the spinel onto the surface of the measuring electrode, followed by firing at 1000° C. for one hour to form a gas diffusion rate-determining layer having a porosity of about 15%.

Figure 15:
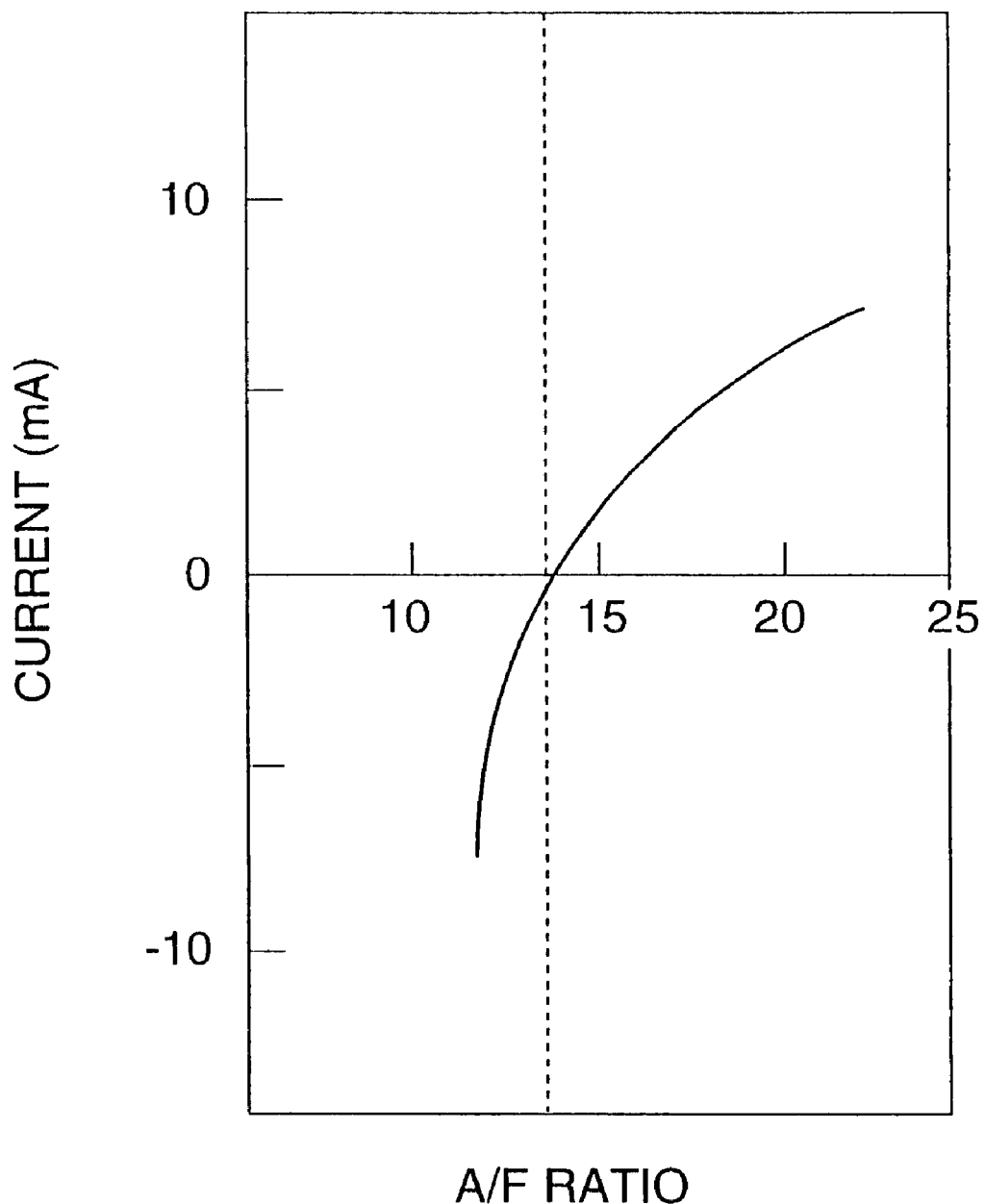
FIG. 15 is a diagram illustrating a relationship between the limit current value of a wide-range AF sensor produced in Example 2 and the A/F ratio.

FIG. 15 illustrates a relationship between the limit current value and the air-fuel ratio of the wide-range air-fuel ratio sensor device at 700° C.

As will be obvious from FIG. 15, the relationship between the limit current value and the air-fuel ratio of the sensor device is represented by a single curve, from which it is learned that the oxygen sensor device of the invention exhibits a function which is enough for detecting the ratio of the air and fuel even in a lean burn region. Further, the oxygen sensor device provided with the gas diffusion rate-determining layer of this example 2 is heated up to 700° C. in 15 seconds like that of Example 1.

(Example 3)

A cylindrically molded article having a closed end and an outer diameter of about 4 mm and in inner diameter of 1 mm was prepared in the same manner as in Example 1.

A conductor pattern (measuring electrode pattern) and a lead pattern of a rectangular shape were formed by using platinum paste on the outer surfaces at opposing positions of the cylindrically molded article. The platinum paste was also applied onto the whole inner surface of the cylindrically molded article to form a conductor pattern (reference electrode pattern). These conductor patterns were so adjusted as to possess a thickness of about 5 $\mu$m after firing.

Further, a green sheet having a thickness of about 200 $\mu$m was prepared by using the slurry that was used for forming the above cylindrically molded article. A first opening portion and a second opening portion of a rectangular shape were formed in the green sheet by punching so as to be in agreement with the pattern of the measuring electrode. The first opening portion and the second opening portion were formed at such positions that they were opposed to each other when the green sheet was wound.

Next, a slurry containing the alumina powder was applied onto the green sheet other than the opening portions maintaining a thickness of about 10 $\mu$m. Further, an electrically conducting paste containing the platinum powder was screen-printed around the first and second opening portions maintaining a thickness of about 10 $\mu$m, thereby to form a heat-generating member pattern on the layer of the alumina slurry. Further, an alumina slurry was applied maintaining a thickness of about 10 $\mu$m onto the layer of the alumina slurry to prepare a laminated sheet for winding incorporating the heat-generating member therein.

The laminated sheet was wound on the surface of the cylindrically molded article via an acrylic resin adhesive to prepare a laminated cylinder. The laminated cylinder was fired in the open air at 1500° C. for 2 hours, and a ceramic protection layer of spinel having a porosity of 30% was formed on the surface of the measuring electrode in the opening portions maintaining a thickness of about 100 $\mu$m by plasma melt-injection thereby to prepare an oxygen sensor device incorporating a heater therein (stoichiometric air-fuel ratio sensor) of the structure shown in FIG. 5.

There was thus obtained the stoichiometric air-fuel ratio sensor device having the first opening portion and the second opening portion of different sizes.

The obtained sensor device was evaluated for its thermal shock resistance in a manner as described below.

That in, the sensor device was heated from room temperature up to 1000° C. in 20 seconds, held at 1000° C. for 60 seconds and was cooled down to room temperature, forming one cycle. This cycle was repeated until the device was broken to find the number of cycles. The results were shown in Table 1 together with the expanding angles $\theta1$ and $\theta2$ of the first and second opening portions of the sensor device.

The numbers of samples were 10 each, and the numbers of cycles until the breakage and the expanding angles were average values of 10 samples each.

TABLE 1

| Sample | Expanding angle (deg) | | Number of cycles until breakage |
|---|---|---|---|
| No. | θ1 | θ2 | (x10⁴) |
| *1 | 35 | none | 13.2 |
| 2 | 22 | 32 | 19.1 |
| 3 | 31 | 34 | 16.3 |
| 4 | 42 | 46 | 20.1 |

TABLE 1-continued

| Sample | Expanding angle (deg) | | Number of cycles until breakage |
|---|---|---|---|
| No. | θ1 | θ2 | (x10⁴) |
| 5 | 55 | 61 | 24.3 |
| 6 | 64 | 61 | 25.1 |
| 7 | 72 | 69 | 21.3 |
| 8 | 91 | 88 | 18.6 |
| 9 | 105 | 113 | 17.5 |
| 10 | 43 | 63 | 22.4 |
| 11 | 54 | 77 | 22.5 |
| 12 | 54 | 25 | 14.5 |

Samples marked with * have one opening portion.

It will be understood from Table 1 that the sensor devices having two sensing portions with first opening portion and second opening portion were broken after the heating cycles of a number larger than that of the sensor device of the sample No. 1 having only one sensing portion, and exhibited excellent thermal shock resistance.

The sample No. 9 which possessed expanding angles of the first and second opening portions of larger than 90° was broken after the heating cycles of an increased number but needed an increased period of time before the sensing portion was heated up to a temperature of 1000° C. Excellent properties were exhibited when the expanding angles of the opening portions were from 30 to 90 degrees and, particularly, from 40 to 70 degrees.

(Example 4)

A cylindrically molded article having a closed end and an outer diameter of about 4 mm and in inner diameter of 1 mm was prepared in the same manner as in Example 1.

A conductor pattern (measuring electrode pattern) and a lead pattern of a rectangular shape were formed by using a platinum paste on the outer surfaces of the cylindrically molded article. The platinum paste was also applied onto the whole inner surface of the cylindrically molded article to form a conductor pattern (reference electrode pattern). These conductor patterns were so adjusted as to possess a thickness of about 5 $\mu$m after firing.

A slurry was prepared by adding an acrylic binder and a toluene solution to the zirconia powder (average particle size of 0.2 $\mu$m) containing 5 mol % of $Y_2O_3$, and was formed into a zirconia green sheet having a thickness of about 200 $\mu$m by the doctor blade method. Electrode patterns for forming a second pair of electrodes were formed on both surfaces of the green sheet at opposing positions.

Thereafter, a slurry containing the aluminum powder was applied by screen-printing onto the zirconia green sheet other than the electrode-forming regions such that the thickness after firing was about 10 $\mu$m. Then, the platinum paste was printed to form a heat-generating member pattern having a thickness after firing of 10 $\mu$m followed by the application of an alumina slurry to bury the heat-generating member pattern thereby to prepare a laminated sheet for winding.

The laminated sheet for winding was wound on the surface of the cylindrically molded article prepared above via an acrylic resin adhesive to prepare a laminated cylinder.

The laminated cylinder was fired in the open air at 1500° C. for 2 hours to obtain an air-fuel ratio sensor device of the invention having the structure shown in FIGS. 6a and 6b.

Further, many sensor devices were prepared while changing the expanding angle θ (see FIG. 12) of the region on where the above-mentioned laminated sheet has not been wound on the cylindrical tube (cylindrically molded article).

The sensor devices were subjected to the temperature cycle repetitively in the same manner as in Example 3. The temperature cycle was repeated 200,000 times to find a probability of breakage of the sensor devices. Table 2 shows the results together with the expansion angle.

The numbers of samples were 100, each. As for the expansion angles of the regions on where the laminated sheet has not been wound, most wide expansion angles of the regions on where the laminated sheet has not been wound were measured from the cross sections of the devices by using an operation-type electron microscope of a low magnification, and were represented by average values of 100 samples.

For comparison, the commercially available flat-plate type oxygen sensor device (sample No. 1) incorporating the heater was also tested in the same manner. The results were as shown in Table 2.

TABLE 2

| Sample No. | Expanding angle (θ) | Probability of breakage (%) | Remarks |
|---|---|---|---|
| 1 | 0 | 92 | flat plate |
| 2 | 5.1 | 42 | cylindrical |
| 3 | 12.4 | 20 | cylindrical |
| 4 | 21.3 | 18 | cylindrical |
| 5 | 28.4 | 28 | cylindrical |
| 7 | 41.6 | 31 | cylindrical |
| 8 | 48.0 | 45 | cylindrical |
| 9 | 61.1 | 62 | cylindrical |

It will be understood from Table 2 that the air-fuel ratio sensor of the present invention is less likely to be broken through heat cycles than the commercially available flat-plate type devices. In particular, the samples are legs broken when they have an expansion angle θ in the region on where the laminated sheet has not been wound of from 5 to 50 degrees. Among them, the samples Nos. 3 and 4 having the expansion angles θ of from 10 to 25 degrees are broken at a probability of smaller than 20%, exhibiting very excellent thermal shock resistance.

(Example 5)

Figure 16:
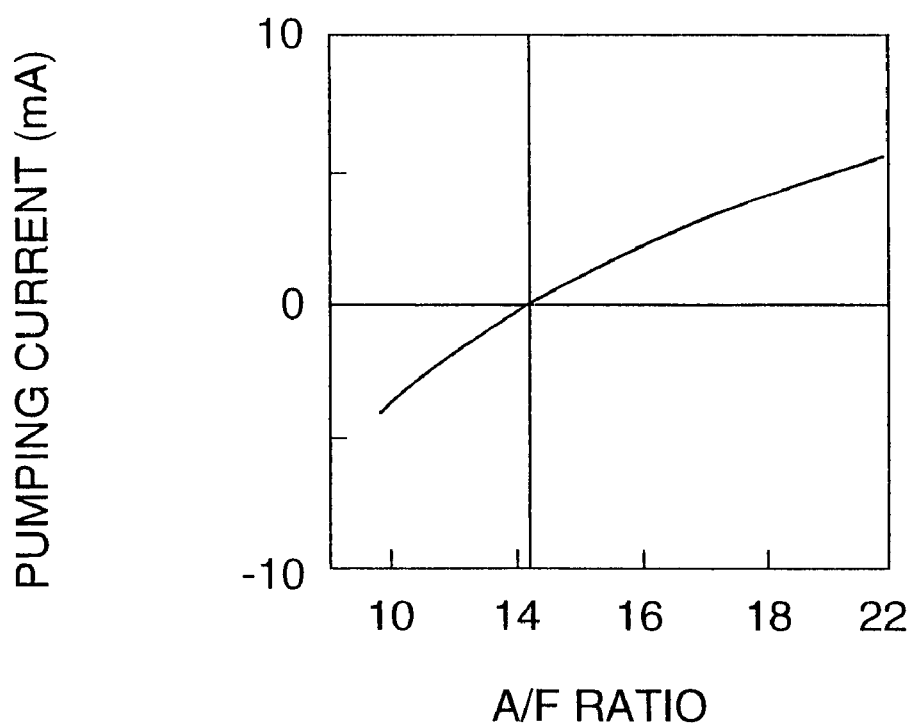
FIG. 16 is a diagram illustrating a relationship between the AF ratio and the pumping current of an oxygen sensor device which is a sample No. 4 produced in Example 4 of when the electromotive force generated across the inner surface and the outer surface of a cylindrical tube is controlled to be 0.5 V at 700° C.

FIG. 16 illustrates a relationship between the pumping current and the air-fuel ratio of the sample No. 4 of Example 4 of when the electromotive force generated by the inner and outer surfaces of the cylindrical tube was adjusted to 0.5 V at 700° C.

It will be understood from FIG. 16 that the relationship between the pumping current and the air-fuel ratio is represented by a single curve. It will thus be understood that the oxygen sensor device exhibits a function which is sufficient for detecting the ratio of the air and fuel even in the combustion region over a wide range.

(Example 6)

A cylindrically molded article having conductor patterns for electrodes on the outer surface and on the inner surface thereof was formed in quite the same manner as in Example 4.

Further, a zirconia green sheet having a thickness of about 80 to 450 μm (the thickness after firing; 55–360 μm) was formed in the same manner as in Example 4 to form electrode patterns that served as a second pair of electrodes on both surfaces of the green sheet at opposing positions.

Thereafter, a slurry containing the alumina powder was applied by screen-printing onto the surface of the zirconia green sheet except the region for forming space (corresponds to opening portion) such that the thickness after firing was about 10 μm.

Then, by using the platinum paste, the heat-generating member pattern was printed on the layer of the alumina slurry such that the thickness after firing was 10 μm, followed by the application with the alumina slurry to bury the heat-generating member therein in order to prepare a laminated sheet for winding.

A filler slurry was prepared by adding a pore-forming agent of an organic resin powder having an average particle diameter of 3 μm, an acrylic binder and a toluene solution to a zirconia powder having an average particle diameter of 2 μm, and was introduced into space formed in the laminated sheet for winding prepared above.

The laminated sheet was wound on the surface of the cylindrically molded article prepared above via an acrylic resin adhesive to prepare a laminated cylinder.

The laminated cylinder was fired in the open air at 1500° C. for 2 hours to obtain an air-fuel ratio sensor device of the invention having the structure shown in FIG. 6b and with its closed opening portion 6 being filled with the porous ceramic (zirconia). The expanding angle θ of a region on where the laminated sheet has not been wound was set to be 25 degrees.

Many sensor devices were prepared as described above having opening portions 6 of different void volumes and having solid electrolyte layers 21 of different thicknesses. The void volume was adjusted by varying the amount of zirconia powder in the filler flurry.

The thus prepared air-fuel sensor devices were subjected to the temperature cycle repeated 200,000 times. Table 3 shows the probabilities of breakage of the devices together with the void volumes in the opening portions 6 and the thicknesses of the solid electrolyte layers 21.

The temperature cycle consisted of elevating the temperature from room temperature up to 1000° C. in 15 seconds and lowering the temperature from 1000° C. down to room temperature. The numbers of samples were 100 each.

The void volume in the opening portion was calculated by the mercury intrusion porosity method, and the thickness of the fixed electrolyte layer was found from a scanning-type electron microphotograph of a magnification of 500 times.

Further, the commercially available flat-plate type oxygen sensor device incorporating the heater that was used for comparison in Example 4, was also tested in the same manner (sample No. 1). The results were as shown in Table 3.

Further, the times (activating time) until a predetermined pumping current was reached were found by maintaining the samples at 700° C. while changing the air-fuel ratio (A/F) from 14(R) to 15(L), and from 15(L) to 14(R) by using $N_2$, $CO_2$, CO, $C_3H_6$ and $O_2$ gases. The results were as shown in Table 3.

TABLE 3

| Sample No. | Void Volume x $10^{-3}$ (mm$^3$) | Thickness of solid electrolyte layer (μm) | Probability of breakage (%) | Response time R→L(ms) | Response time L→R(ms) |
|---|---|---|---|---|---|
| *1 | — | — | 100 | 370 | 430 |
| 2 | 8 | 210 | 22 | — | — |
| 3 | 22 | 203 | 25 | 132 | 145 |
| 4 | 43 | 191 | 29 | 134 | 168 |
| 5 | 67 | 201 | 35 | 155 | 167 |
| 6 | 89 | 188 | 44 | 167 | 180 |
| 7 | 98 | 204 | 47 | 223 | 278 |
| 8 | 146 | 205 | 64 | 340 | 389 |
| 9 | 55 | 82 | 88 | 144 | 178 |
| 10 | 64 | 105 | 47 | 157 | 189 |
| 11 | 51 | 153 | 37 | 178 | 227 |
| 12 | 44 | 205 | 20 | 226 | 267 |
| 13 | 63 | 248 | 17 | 278 | 321 |
| 14 | 47 | 296 | 18 | 325 | 389 |
| 15 | 53 | 342 | 22 | 335 | 398 |
| 16 | 51 | 447 | 33 | 529 | 631 |

Samples marked with * have no solid electrolyte layer and have their opening portions not closed.

It will be understood from Table 3 that the solid electrolyte layers are likely to be broken through heat cycles in the sample No. 8 having a void volume of not smaller than $100 \times 10^{-3}$ mm$^3$ and in the sample No. 9 having the solid electrolyte layer of a thickness of not larger than 100 μm.

On the other hand, the sensor devices having void volumes of not larger than $100 \times 10^{-3}$ mm$^3$ and solid electrolyte layers of thicknesses of not smaller than 100 μm are very little broken, exhibiting excellent thermal shock resistance compared with the flat-plate type devices placed in the market and with the conventional cylindrical devices.

The sample No. 2 having a void volume of not larger than $20 \times 10^{-3}$ mm$^3$ exhibited a quick gas response but exhibited a small change in the current relative to a change in the air-fuel ratio (A/F) and, hence, its change in the A/F ratio could not be accurately measured. Further, the sample No. 16 having a solid electrolyte layer of a thickness in excess of 350 μm exhibited a poor electric conductivity through the solid electrolyte layer and, hence, exhibited a poor gas response.

From the standpoint of gas response and the device strength shown in Table 3, it is obvious that excellent results are obtained when the void volume is within a range of from $20 \times 10^{-3}$ to $100 \times 10^{-3}$ mm$^3$ when the opening portion 6 is filled with the porous ceramic. It is further obvious that excellent results are obtained when the solid electrolyte layer has a thickness within a range of from 100 to 350 μm.

(Example 7)

Figure 17:
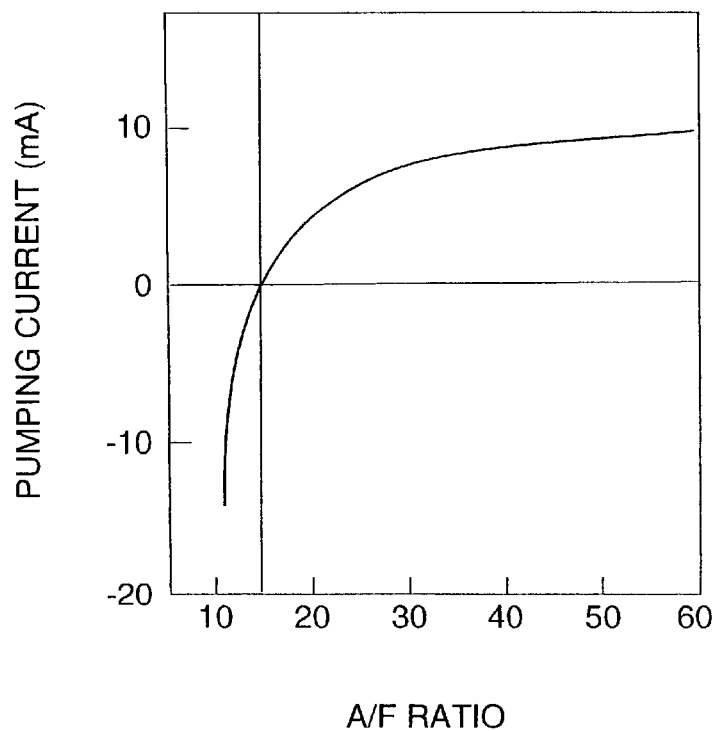
FIG. 17 is a diagram illustrating a relationship between the air-fuel ratio (A/F) of an oxygen sensor device which is a sample No. 5 produced in Example 6 at a temperature of 700° C. and the pumping current value of a solid electrolyte layer necessary for maintaining the oxygen concentration in space constant (450 mV)
Figure 18:
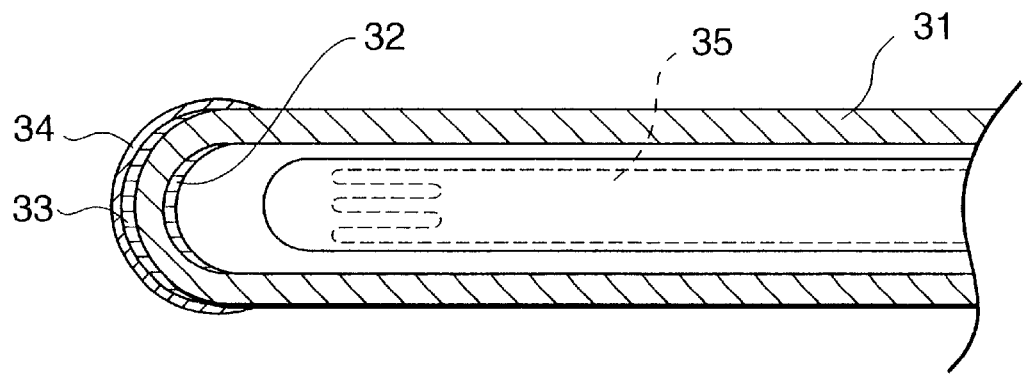
FIG. 18 is a sectional view schematically illustrating a widely known cylindrical oxygen sensor.

FIG. 17 shows a pumping current of the solid electrolyte layer necessary for maintaining the oxygen concentration in space constant (450 mV) when the sample No. 5 of Example 6 is maintained at 700° C. and the air-fuel ratio (A/F) is changed by using $N_2$, $CO_2$, CO, $C_3H_6$ and $O_2$ gases. The obtained pumping currents were plotted on a single curve over an air-fuel ratio region of from 10 to 60.

It will thus be understood that the sensor device of the invention exhibits excellent performance for accurately controlling the air-fuel ratio over a wide air-fuel ratio region.

What is claimed is:

1. An oxygen sensor device comprising:
   a cylindrical tube of a ceramic solid electrolyte having an oxygen ion conducting property and with its one end being closed;
   a reference electrode on an inner surface of said cylindrical tube; and
   a measuring electrode on an outer surface of said cylindrical tube at a position at least partially opposed to said reference electrode; and
   a ceramic layer on the outer surface of said cylindrical tube, said ceramic layer defining an opening portion and said ceramic layer incorporating a heat-generating member therein;
   wherein said opening portion in said ceramic layer is formed at such a position that at least a portion of said measuring electrode is exposed therein; and
   wherein said heat-generating member is buried in said ceramic layer at a position at least near said measuring electrode.

2. An oxygen sensor device according to claim 1, wherein said heat-generating member is buried around said opening portion.

3. An oxygen sensor device according to claim 1, wherein said cylindrical tube and said ceramic layer incorporating said heat-generating member therein are formed by the co-firing.

4. An oxygen sensor device according to claim 1, wherein a porous ceramic layer is formed on the surface of said measuring electrode.

5. An oxygen sensor device according to claim 1, wherein:
   a solid electrolyte layer having an oxygen ion conducting property is formed on said ceramic layer incorporating said heat-generating member therein and extending in a manner to close said opening portion;
   an outer electrode and an inner electrode are provided being opposed to each other on said opening portion with said solid electrolyte layer sandwiched therebetween; and
   space closed by said solid electrolyte layer is communicated with the exterior through a diffusing hole for introducing a gas to be measured.

6. An oxygen sensor device according to claim 5, wherein a sensing cell is formed by said cylindrical tube and by the pair of said reference electrode and said measuring electrode.

7. An oxygen sensor device according to claim 5, wherein a pumping cell is formed by said solid electrolyte layer and by the pair of said outer electrode and said inner electrode.

8. An oxygen sensor device according to claim 5, wherein said diffusing hole is formed in said solid electrolyte layer.

9. An oxygen sensor device according to claim 5, wherein said diffusing hole is formed in said ceramic layer incorporating said heat-generating member therein.

10. An oxygen sensor device according to claim 5, wherein said ceramic layer incorporating said heat-generating member therein and said solid electrolyte layer are formed by being wound on a portion of said cylindrical tube.

11. An oxygen sensor device according to claim 10, wherein a region on the outer surface of said cylindrical tube on where neither said ceramic layer incorporating the heat-generating member nor said solid electrolyte layer is wound, has a width forming an expanding angle of from 5 to 50 degrees from the center of said cylindrical tube as viewed on a lateral cross section thereof.

12. An oxygen sensor device according to claim 5, wherein said solid electrolyte layer has a thickness of from 100 to 350 μm, and space in said opening portion closed by said solid electrolyte layer is filled with a porous ceramic such that the void volume is from $20 \times 10^{-3}$ to $100 \times 10^{-3}$ mm$^3$.

13. An oxygen sensor device according to claim 1, wherein at least two opening portions are formed in said ceramic layer incorporating the heat-generating member therein, said two opening portions being opposed to each other sandwiching the center of the cylindrical tube therebetween.

14. An oxygen sensor device according to claim 12, wherein said two opening portions have such widths that the expansion angles from the center of said cylindrical tube are from 30 to 90 degrees as viewed on a lateral cross section thereof.

* * * * *